US012168135B2

(12) United States Patent
Opie et al.

(10) Patent No.: US 12,168,135 B2
(45) Date of Patent: Dec. 17, 2024

(54) METHODS, SYSTEMS, AND APPARATUS FOR CLOSED-LOOP NEUROMODULATION

(71) Applicants: Synchron Australia Pty Limited, Melbourne (AU); The University of Melbourne, The University of Melbourne (AU)

(72) Inventors: Nicholas Lachlan Opie, Melbourne (AU); Thomas James Oxley, New York, NY (US); Gil Simon Rind, Parkville (AU)

(73) Assignees: Synchron Australia Pty Limited, Melbourne (AU); The University of Melbourne, Melbourne (AU)

( * ) Notice: Subject to any disclaimer, the term of this patent is extended or adjusted under 35 U.S.C. 154(b) by 0 days.

(21) Appl. No.: 18/309,073

(22) Filed: Apr. 28, 2023

(65) Prior Publication Data

US 2023/0302282 A1 Sep. 28, 2023

Related U.S. Application Data

(60) Division of application No. 17/659,381, filed on Apr. 15, 2022, now Pat. No. 11,672,986, which is a
(Continued)

(51) Int. Cl.
*A61N 1/36* (2006.01)
*A61N 1/375* (2006.01)
*A61N 1/378* (2006.01)

(52) U.S. Cl.
CPC ..... *A61N 1/36189* (2013.01); *A61N 1/36053* (2013.01); *A61N 1/36064* (2013.01);
(Continued)

(58) Field of Classification Search
CPC ............ A61N 1/36189; A61N 1/37516; A61N 1/37514; A61N 1/36053; A61N 1/36064; A61N 1/36175; A61N 1/3787
See application file for complete search history.

(56) References Cited

U.S. PATENT DOCUMENTS 4,146,029 A * 3/1979 Ellinwood, Jr. .... A61N 1/37211
607/9
4,390,020 A * 6/1983 Herpers ............. A61N 1/37217
607/29
(Continued)

FOREIGN PATENT DOCUMENTS

| JP | 2019-524389 | 9/2019 |
|---|---|---|
| WO | WO 2021/092462 | 5/2021 |
| WO | WO 2021/097448 | 5/2021 |

OTHER PUBLICATIONS

"Implant" definition from the NIH, https://www.cancer.gov/publications/dictionaries/cancer-terms/def/implant (Year: 2022), 1 page.
(Continued)

*Primary Examiner* — Eric D. Bertram
(74) *Attorney, Agent, or Firm* — Levine Bagade Han LLP

(57) ABSTRACT

Systems, apparatus, and methods for treating medication refractory epilepsy are disclosed. In one embodiment, a method of treating epilepsy is disclosed comprising detecting, using a first electrode array coupled to a first endovascular carrier, an electrophysiological signal of a subject. The method further comprises analyzing the electrophysiological signal using a neuromodulation unit electrically coupled to the first electrode array and stimulating an intracorporeal target of the subject using a second electrode array coupled to a second endovascular carrier implanted within a part of a bodily vessel superior to a base of the skull of the subject.

5 Claims, 18 Drawing Sheets

Related U.S. Application Data division of application No. 17/398,854, filed on Aug. 10, 2021, now Pat. No. 11,883,671, which is a continuation of application No. PCT/US2020/059509, filed on Nov. 6, 2020.

(60) Provisional application No. 63/062,633, filed on Aug. 7, 2020.

(52) U.S. Cl.
CPC ..... *A61N 1/36175* (2013.01); *A61N 1/37514* (2017.08); *A61N 1/37516* (2017.08); *A61N 1/3787* (2013.01)

(56) References Cited

U.S. PATENT DOCUMENTS

| | | | | |
|---|---|---|---|---|
| 4,699,143 | A * | 10/1987 | Dufresne | A61N 1/36034 |
| | | | | 607/46 |
| 6,154,675 | A * | 11/2000 | Juran | A61N 1/3708 |
| | | | | 607/27 |
| 6,360,122 | B1 * | 3/2002 | Fischell | A61N 1/3605 |
| | | | | 600/544 |
| 6,381,496 | B1 * | 4/2002 | Meadows | A61N 1/36128 |
| | | | | 607/59 |
| 6,480,743 | B1 * | 11/2002 | Kirkpatrick | A61N 1/36135 |
| | | | | 607/45 |
| 6,493,586 | B1 * | 12/2002 | Stahmann | A61N 1/3706 |
| | | | | 607/27 |
| 7,089,059 | B1 * | 8/2006 | Pless | A61B 5/7203 |
| | | | | 607/45 |
| 7,574,259 | B1 * | 8/2009 | Pei | A61N 1/39622 |
| | | | | 607/28 |
| 8,396,560 | B2 * | 3/2013 | Libbus | A61N 1/36171 |
| | | | | 607/44 |
| 10,485,968 | B2 | 11/2019 | Opie et al. | |
| 10,512,555 | B2 | 12/2019 | John et al. | |
| 10,575,783 | B2 | 3/2020 | Oxley | |
| 10,729,530 | B2 | 8/2020 | Opie et al. | |
| 2003/0144711 | A1 * | 7/2003 | Pless | A61N 1/36135 |
| | | | | 607/60 |
| 2003/0153959 | A1 | 8/2003 | Thacker | A61N 1/36071 |
| | | | | 607/48 |
| 2004/0199210 | A1 * | 10/2004 | Shelchuk | A61N 1/36114 |
| | | | | 607/17 |
| 2005/0075683 | A1 * | 4/2005 | Miesel | A61N 1/37211 |
| | | | | 607/60 |
| 2005/0137646 | A1 * | 6/2005 | Wallace | A61N 1/0529 |
| | | | | 607/45 |
| 2005/0137647 | A1 * | 6/2005 | Wallace | A61N 1/0531 |
| | | | | 607/45 |
| 2005/0187589 | A1 * | 8/2005 | Wallace | A61N 1/36017 |
| | | | | 607/45 |
| 2005/0267542 | A1 * | 12/2005 | David | A61N 1/3622 |
| | | | | 607/17 |
| 2006/0020297 | A1 * | 1/2006 | Gerber | A61N 1/36071 |
| | | | | 607/39 |
| 2006/0058854 | A1 * | 3/2006 | Abrams | A61N 1/36082 |
| | | | | 607/45 |
| 2006/0095080 | A1 * | 5/2006 | Libbus | A61N 1/37211 |
| | | | | 607/9 |
| 2006/0206159 | A1 * | 9/2006 | Moffitt | A61N 1/3962 |
| | | | | 607/37 |
| 2006/0259083 | A1 * | 11/2006 | Libbus | A61N 1/36564 |
| | | | | 607/9 |
| 2006/0271151 | A1 * | 11/2006 | McGarry | A61M 25/1011 |
| | | | | 623/1.11 |
| 2007/0150006 | A1 | 6/2007 | Libbus et al. | |
| 2007/0276461 | A1 * | 11/2007 | Andreas | A61F 2/958 |
| | | | | 623/1.11 |
| 2009/0276025 | A1 | 11/2009 | Burnes et al. | |
| 2010/0016929 | A1 * | 1/2010 | Prochazka | A61B 5/0028 |
| | | | | 607/72 |
| 2011/0112601 | A1 | 5/2011 | Meadows et al. | |
| 2014/0046407 | A1 | 2/2014 | Ben-Ezra et al. | |
| 2014/0277256 | A1 * | 9/2014 | Osorio | A61N 1/37235 |
| | | | | 607/45 |
| 2014/0288667 | A1 | 9/2014 | Oxley | |
| 2015/0012071 | A1 | 1/2015 | Bradley et al. | |
| 2015/0374991 | A1 | 12/2015 | Morris et al. | |
| 2016/0220821 | A1 | 8/2016 | O'Connell et al. | |
| 2018/0036533 | A1 | 2/2018 | Yoo | |
| 2018/0236221 | A1 | 8/2018 | Opie et al. | |
| 2018/0303595 | A1 * | 10/2018 | Opie | A61F 2/90 |
| 2019/0038438 | A1 * | 2/2019 | John | G06F 3/015 |
| 2019/0091475 | A1 * | 3/2019 | Pachon-Mateos | A61N 1/36114 |
| 2019/0274855 | A1 * | 9/2019 | Pate | A61F 2/82 |
| 2019/0336748 | A1 | 11/2019 | Oxley | |
| 2020/0016396 | A1 | 1/2020 | Yoo | |
| 2020/0023189 | A1 * | 1/2020 | Gribetz | A61N 1/36196 |
| 2020/0078195 | A1 | 3/2020 | John et al. | |
| 2020/0363869 | A1 | 11/2020 | Yoo | |
| 2021/0361950 | A1 | 11/2021 | Opie et al. | |
| 2022/0241596 | A1 | 8/2022 | Opie et al. | |
| 2024/0099825 | A1 * | 3/2024 | Opie | A61N 1/0529 |

OTHER PUBLICATIONS

"Implants and Prosthetics" definition from the FDA, https://www.fda.gov/medical-devices/products-and-medical-procedures/implants-and-prosthetics (Year: 2019), 2 pages.

Arya, R. et al. "Adverse events related to extraoperative invasive EEG monitoring with subdural grid electrodes: a systematic review and meta-analysis," *Epilepsia*, vol. 54, pp. 828-839, May 2013.

Ball, T. et al. "Signal quality of simultaneously recorded invasive and non-invasive EEG," *NeuroImage*, vol. 46, pp. 708-716, Jul. 1, 2009.

Bano, S. et al. "Measurement of internal jugular vein and common carotid artery diameter ratio by ultrasound to estimate central venous pressure," *Cureus*, 10 pages, Mar. 2018.

Benedetti-Isaac, J. et al. "Seizure frequency reduction after posteromedial hypothalamus deep brain stimulation in drug-resistant epilepsy associated with intractable aggressive behavior," *Epilepsia*, vol. 56, pp. 1152-1161, Jul. 2015.

Bergey, G. et al. "Long-term treatment with responsive brain stimulation in adults with refractory partial seizures," *Neurology*, vol. 84, pp. 810-817, Feb. 24, 2015.

Bigelow, M. et al. "Neural stimulation systems for the control of refractory epilepsy: a review," *Journal of Neuroengineering and Rehabilitation*, vol. 16, pp. 126, Oct. 29, 2019.

Boddu, S. et al. "Anatomic measurements of cerebral venous sinuses in idiopathic intracranial hypertension patients," *PloS One*, vol. 13, 10 pages, Jun. 1, 2018.

Boëx, C. et al. "Chronic deep brain stimulation in mesial temporal lobe epilepsy," *Seizure*, vol. 20, pp. 485-490, Jul. 2011.

Bondallaz, P. et al. "Electrode location and clinical outcome in hippocampal electrical stimulation for mesial temporal lobe epilepsy," *Seizure*, vol. 22, pp. 390-395, Jun. 2013.

Boniface, S. "Endovascular electroencephalography: the technique and its application during carotid amytal assessment," *Journal of Neurology, Neurosurgery & Psychiatry*, vol. 62, pp. 193-195, Feb. 1997.

Boon, P. et al. "A prospective, multicenter study of cardiac-based seizure detection to activate vagus nerve stimulation," *Seizure*, vol. 32, pp. 52-61, Nov. 2015.

Bower, M. et al. "Intravenous recording of intracranial, broadband EEG," *J Neurosci Methods*, vol. 214, pp. 21-26, Mar. 30, 2013.

Bullard, A. et al. "Estimating Risk for Future Intracranial, Fully Implanted, Modular Neuroprosthetic Systems: A Systematic Review of Hardware Complications in Clinical Deep Brain Stimulation and Experimental Human Intracortical Arrays," *Neuromodulation: Technology at the Neural Interface*, vol. 23, pp. 411-426, Jun. 2020.

Butson, C. et al. "Sources and effects of electrode impedance during deep brain stimulation," *Clinical Neurophysiology*, vol. 117, pp. 447-454, Feb. 2006.

(56) References Cited

OTHER PUBLICATIONS

Chang, C. et al. "Electrical cortical stimulation for refractory focal epilepsy: A long-term follow-up study," *Epilepsy Research*, vol. 151, pp. 24-30, Mar. 2019.

Chaynes, P. "Microsurgical anatomy of the great cerebral vein of Galen and its tributaries," *Journal of Neurosurgery*, vol. 99, pp. 1028-1038, Dec. 2003.

Chen, W. et al. "Heart rate changes in partial seizures: analysis of influencing factors among refractory patients," *BMC Neurology*, vol. 14, p. 135, Jun. 20, 2014.

Claassen, J. et al. "Detection of electrographic seizures with continuous EEG monitoring in critically ill patients," *Neurology*, vol. 62, pp. 1743-1748, May 2004.

Clenaghan, S. et al. "Relationship between Trendelenburg tilt and internal jugular vein diameter," *Emergency Medicine Journal*, vol. 22, pp. 867-868, Nov. 18, 2005.

Coffey, R. "Deep Brain Stimulation Devices: A Brief Technical History and Review," *Artificial Organs*, vol. 33, pp. 208-220, Mar. 2009.

Cook, M. et al. "Prediction of seizure likelihood with a long-term, implanted seizure advisory system in patients with drug-resistant epilepsy: a first-in-man study," *The Lancet Neurology*, vol. 12, pp. 563-571, Jun. 2013.

Cukiert, A. et al. "Seizure outcome after hippocampal deep brain stimulation in patients with refractory temporal lobe epilepsy: A prospective, controlled, randomized, double-blind study," *Epilepsia*, vol. 58, pp. 1728-1733, Oct. 2017.

Cyberonics. VNS Therapy System Physician's Manual. In Editor (Ed)(Eds) Book VNS Therapy System Physician's Manual, Cyberonics Houston, TX; 1 page, May 2015.

D'Alessandro, M. et al. "Epileptic seizure prediction using hybrid feature selection over multiple intracranial EEG electrode contacts: a report of four patients," *IEEE Transactions on Biomedical Engineering*, vol. 50, pp. 603-615, May 13, 2003.

Davis, R. "Cerebellar Stimulation for Seizure Control: 17-Year Study," *Stereotactic and Functional Neurosurgery*, vol. 58, 4 pages, Abstract only, 1992.

Davis, R. et al. "Cerebellar Stimulation for Seizure Control," In Lozano AM, Gildenberg PL, Tasker RR (Eds) Textbook of Stereotactic and Functional Neurosurgery, Springer Berlin Heidelberg: Berlin, Heidelberg; pp. 2823-2837, 2009.

Deniz, C. et al. "Comparative evaluation of dural venous sinuses and cerebral veins using contrast-enhanced spoiled gradient recalled echo and time-of-flight magnetic resonance venography," *Journal of Contemporary Medicine*, vol. 9, Aug. 2019.

Di Giacopo, A. et al. "Selective deep brain stimulation in the substantia nigra reduces myoclonus in progressive myoclonic epilepsy: a novel observation and short review of the literature," *Epileptic Disorders*, vol. 21, pp. 283-288, Jun. 2019.

Durst, C. et al. "Prevalence of dural venous sinus stenosis and hypoplasia in a generalized population," *Journal of Neurointerventional Surgery*, vol. 8, pp. 1173-1177, Oct. 2016.

Elliott, R. et al. "Vagus nerve stimulation in 436 consecutive patients with treatment-resistant epilepsy: long-term outcomes and predictors of response," *Epilepsy & Behavior*, vol. 20, pp. 57-63, Jan. 2011.

Feigin, VL et al. "Global, regional, and national burden of neurological disorders, 1990-2016: a systematic analysis for the Global Burden of Disease Study 2016," *The Lancet Neurology*, 18(5), pp. 459-480, Mar. 14, 2019.

Fisher, R. et al. "Automatic vagus nerve stimulation triggered by ictal tachycardia: clinical outcomes and device performance—the US E-37 trial," *Neuromodulation: Technology at the Neural Interface*, vol. 19, pp. 188-195, Feb. 2016.

Fisher, R. et al. "Electrical stimulation of the anterior nucleus of thalamus for treatment of refractory epilepsy," *Epilepsia*, vol. 51, pp. 899-908, May 2010.

Fountas, K. et al. "Cerebellar stimulation in the management of medically intractable epilepsy: a systematic and critical review," *Neurosurgical Focus*, vol. 29:E8, Aug. 2010.

Franzini, A. et al. "Deep brain stimulation of two unconventional targets in refractory non-resectable epilepsy," *Stereotactic and Functional Neurosurgery*, vol. 86, Abstract, 10 pages, Dec. 2008.

Freeman, W. et al. "Spatial spectral analysis of human electrocorticograms including the alpha and gamma bands," *J Neurosci Methods*, vol. 95, pp. 111-121, Feb. 2000.

Gerboni, G. et al. "Cortical Brain Stimulation with Endovascular Electrodes," 2018 40th Annual International Conference of the IEEE Engineering in Medicine and Biology Society, *IEEE*, pp. 3088-3091, Jul. 18-21, 2018.

Gotman, J. "Automatic recognition of epileptic seizures in the EEG," *Electroencephalography and Clinical Neurophysiology*, vol. 54, pp. 530-540, Nov. 1982.

Hamilton, P. et al. "Clinical outcomes of VNS therapy with AspireSR®(including cardiac-based seizure detection) at a large complex epilepsy and surgery centre," *Seizure*, vol. 58, pp. 120-126, May 2018.

Hedegärd, E. et al. "Complications to invasive epilepsy surgery workup with subdural and depth electrodes: a prospective population-based observational study," *Journal of Neurology, Neurosurgery & Psychiatry*, vol. 85, pp. 716-720, Jul. 2014.

Houck, A. et al. "Increased diameters of the internal cerebral veins and the basal veins of rosenthal are associated with white matter hyperintensity volume," *American Journal of Neuroradiology*, vol. 40, pp. 1712-1718, Oct. 2019.

Jansen, K. et al. "Cardiac changes in epilepsy," *Seizure*, vol. 19, pp. 455-460, Oct. 2010.

Jin, H. et al. "Hippocampal deep brain stimulation in nonlesional refractory mesial temporal lobe epilepsy," Seizure, vol. 37, pp. 1-7, Apr. 2016.

John, S. et al. "In vivo impedance characterization of cortical recording electrodes shows dependence on electrode location and size," *IEEE Transactions on Biomedical Engineering*, vol. 66, pp. 675-681, Jul. 10, 2018, John, S. et al. "Signal quality of simultaneously recorded endovascular, subdural and epidural signals are comparable," *Scientific Reports*, vol. 8, pp. 1-12, May 30, 2018.

Klinger, N. et al. "Deep brain stimulation for seizure control in drug-resistant epilepsy," *Neurosurgical focus*, 45(2):E4, Aug. 2018.

Kossoff, E. et al. "Effect of an external responsive neurostimulator on seizures and electrographic discharges during subdural electrode monitoring," *Epilepsia*, vol. 45, pp. 1560-1567, Dec. 2004.

Koubeissi, M. et al. "Low-frequency electrical stimulation of a fiber tract in temporal lobe epilepsy," *Annals of Neurology*, vol. 74, pp. 223-231, Aug. 2013.

Kowski, A. et al. "Nucleus accumbens stimulation in partial epilepsy—a randomized controlled case series," *Epilepsia*, vol. 56:e78-e82, Jun. 2015.

Kunieda, T. et al. "Use of cavernous sinus EEG in the detection of seizure onset and spread in mesial temporal lobe epilepsy," *Epilepsia*, vol. 41, pp. 1411-1419, Nov. 2000.

Kwan, P. et al. "Early identification of refractory epilepsy," *New England Journal of Medicine*, 342(5), pp. 314-319, Feb. 3, 2000.

Legon, W. et al. "Neuromodulation with single-element transcranial focused ultrasound in human thalamus," *Human Brain Mapping*, vol. 39, pp. 1995-2006, Jan. 2018.

Leishangthem, L. et al. "Dural venous sinus stenting for idiopathic intracranial hypertension: An updated review," *Journal of Neuroradiology*, vol. 46, pp. 148-154, Mar. 2019.

Leutmezer, F. et al. "Electrocardiogramges at the onset of epileptic seizures," *Epilepsia*, vol. 44, pp. 348-354, Mar. 7, 2003.

Levitt, M. et al. "Venous sinus stenting in patients without idiopathic intracranial hypertension," *J Neurointerv Surg* vol. 9, pp. 512-515, May 2017.

Li, M. et al. "Deep brain stimulation for drug-resistant epilepsy," *Epilepsia*, vol. 59, pp. 273-290, Feb. 2018.

Litt, B. et al. "Epileptic seizures may begin hours in advance of clinical onset: a report of five patients," *Neuron*, vol. 30, pp. 51-64, Apr. 2001.

Litt, B. et al. "Prediction of epileptic seizures," *The Lancet Neurology*, vol. 1, pp. 22-30, May 2002.

LivaNova. VNS Therapy System Epilepsy Physician's Manual, US Version, 164 pages, Jan. 2020.

(56) References Cited

OTHER PUBLICATIONS

Llinás, R. et al. "Neuro-vascular central nervous recording/stimulating system: using nanotechnology probes," *J Nanopart Res*, vol. 7, pp. 111-127, Jun. 2005.
Mormann, F. et al. "Seizure anticipation: from algorithms to clinical practice," *Current Opinion in Neurology*, vol. 19, pp. 187-193, Apr. 2006.
Morrell, M. "Responsive cortical stimulation for the treatment of medically intractable partial epilepsy," *Neurology*, vol. 77 pp. 1295-1304, Sep. 27, 2011.
Morrell, M. et al. "Brain stimulation for epilepsy: can scheduled or responsive neurostimulation stop seizures?" *Current Opinion in Neurology*, vol. 19, pp. 164-168, Apr. 2006.
Morrell, M., "Nine-year prospective safety and effectiveness outcomes from the long-term treatment trial of the RNS system," *Brain Stimulation Abstracts Only*, vol. 12, p. 469, Mar. 1, 2019.
Nowinski, W. "3D Atlas of the Brain, Head and Neck in 2953 pieces," *Neuroinformatics*, vol. 15, pp. 395-400, Oct. 2017.
Nowinski, W. et al. "Simulation and assessment of cerebrovascular damage in deep brain stimulation using a stereotactive atlas of vasculature and structure derived from multiple 3- and 7-tesla scans," *J. Neurosurg*, vol. 113, pp. 1234-1241, Dec. 2010.
Opie, N. et al. "Chronic impedance spectroscopy of an endovascular stent-electrode array," *Journal of Neural Engineering*, vol. 13, pp. 1-10, Jul. 5, 2016.
Opie, N. et al. "Feasibility of a chronic, minimally invasive endovascular neural interface," 2016 38th Annual International Conference of the IEEE Engineering in Medicine and Biology Society, *IEEE*, pp. 4455-4458, Aug. 16-20, 2016.
Opie, N. et al. "Heating of the eye by a retinal prosthesis: modeling, cadaver and in vivo study," *IEEE Transactions on Biomedical Engineering*, vol. 59, pp. 339-345, Feb. 2012.
Opie, N. et al. "Micro-CT and histological evaluation of an neural interface implanted within a blood vessel," *IEEE Trans Biomed Eng*, vol. 64, pp. 928-934, Apr. 2017.
Opie, N. et al. "Neural Stimulation with an Endovascular Brain-Machine Interface," *9th International IEEE EMBS Conference on Neural Engineering*, pp. 738-741, Mar. 20-23, 2019.
Opie, N. et al. "Retinal prosthesis safety: alterations in microglia morphology due to thermal damage and retinal implant contact," *Investigative Ophthalmology & Visual Science*, vol. 53, pp. 7802-7812, Nov. 2012.
Opie, NL et al. "Focal stimulation of the sheep motor cortex with a chronically implanted minimally invasive electrode array mounted on an endovascular stent," *Nature Biomedical Engineering*, vol. 2, pp. 907-914, Dec. 3, 2018.
Osorio, O. et al. "Automated seizure abatement in humans using electrical stimulation," *Annals of Neurology*, vol. 57, pp. 258-268, Feb. 2005.
Oxley, T. et al. "An ovine model of cerebral catheter venography for implantation of an endovascular neural interface," *Journal of Neurosurgery*, vol. 128, pp. 1020-1027, Apr. 2018.
Oxley, T. et al. "LB-008 Motor neuroprosthesis implanted using cerebral venography improves activities of daily living in severe paralysis," *Journal of Neurointerventional Surgery*, vol. 12, pp. A165-A166, Aug. 2020.
Oxley, T. et al. "Minimally invasive endovascular stent-electrode array for high-fidelity, chronic recordings of cortical neural activity," *Nat Biotechnol*, vol. 34, pp. 320-327, Mar. 2016.
Öztoprak, B. "Prominent cerebral veins on susceptibility-weighted imaging (SWI) in pulmonary embolism," *European Radiology*, vol. 27, pp. 3004-3012, Jul. 2017.
Penn, R. et al. "Intravascular intracranial EEG recording," *J Neurosurg*, vol. 38, pp. 239-243, Feb. 1973.
Rajah, G. et al. "Endovascular delivery of leads and stentrodes and their applications to deep brain stimulation and neuromodulation: a review," *Neurosurgical Focus*, vol. 45:E19, Aug. 2018.
Raza, S. et al. "Endovascular Neuromodulation: Safety Profile and Future Directions," *Frontiers in Neurology*, vol. 11, pp. 1-10, Apr. 24, 2020.
Révész, D. et al. "Complications and safety of vagus nerve stimulation: 25 years of experience at a single center," Journal of Neurosurgery: *Pediatrics*, vol. 18, pp. 97-104, Jul. 2016.
Salanova, V. et al. "Long-term efficacy and safety of thalamic stimulation for drug-resistant partial epilepsy," *Neurology*, vol. 84, pp. 1017-1025, Mar. 10, 2015.
Schmidt, R. et al. "Complications of subdural and depth electrodes in 269 patients undergoing 317 procedures for invasive monitoring in epilepsy," *Epilepsia*, vol. 57, pp. 1697-1708, Oct. 2016.
Schmitt, F. et al. "Safety and feasibility of nucleus accumbens stimulation in five patients with epilepsy," *Journal of Neurology*, vol. 261, pp. 1477-1484, May 7, 2014.
Schwartz, A. et al. "Brain-controlled interfaces: movement restoration with neural prosthetics," *Neuron*, vol. 52, pp. 205-220, Oct. 5, 2006.
Sevcencu, C. et al. "Autonomic alterations and cardiac changes in epilepsy," *Epilepsia*, vol. 51, pp. 725-737, May 2010.
Sheriff, F. et al. "Dual Antiplatelet Therapy Duration After Venous Sinus Stenting for Idiopathic Intracranial Hypertension and Stent Survival—Is Longer Necessarily Better? A Meta-Regression," *World Neurosurgery*, vol. 151, pp. e86-e93, Jul. 2021.
Sprengers, M. et al. "Deep brain and cortical stimulation for epilepsy," *Cochrane Database of Systematic Reviews*, 96 pages, Jul. 18, 2017.
Springer, U. et al. "Long-term Habituation of the Smile Response with Deep Brain Stimulation," *Neurocase*, vol. 12, pp. 191-196, Feb. 2006.
Staba, R. et al. "Quantitative analysis of high-frequency oscillations (80-500 Hz) recorded in human epileptic hippocampus and entorhinal cortex," *Journal of neurophysiology*, vol. 88, pp. 743-1752, Oct. 2002.
Stoeter, P. et al. "Intracranial electroencephalographic and evoked-potential recording from intravascular guide wires," *Am J Neuroradiology*, vol. 16, pp. 1214-1217, Jun. 1995.
Sun, F. et al. "Closed-loop Neurostimulation: The Clinical Experience," *Neurotherapeutics*, vol. 11, pp. 553-563, May 22, 2014.
Sun, F. et al. "Responsive cortical stimulation for the treatment of epilepsy," *Neurotherapeutics*, vol. 5, pp. 68-74, Jan. 2008.
Tellez-Zenteno, J. et al. "Hippocampal electrical stimulation in mesial temporal lobe epilepsy," *Neurology* vol. 66, pp. 1490-1494, May 23, 2006.
Teplitzky, B. et al. "Computational modeling of an endovascular approach to deep brain stimulation," *J Neural Eng*, vol. 11, pp. 026011, Mar. 10, 2014.
Turk, A. "Use of self-expanding stents in distal small cerebral vessels," *American Journal of Neuroradiology*, vol. 28, pp. 533-536, Mar. 2007.
Vonck, K. et al. "A decade of experience with deep brain stimulation for patients with refractory medial temporal lobe epilepsy," *International Journal of Neural Systems*, vol. 23:1250034, Feb. 2013.
Wang, H. et al. "Predictors of seizure reduction outcome after vagus nerve stimulation in drug-resistant epilepsy," *Seizure*, vol. 66, pp. 53-60, Mar. 2019.
Wheless, J. et al. "Vagus nerve stimulation (VNS) therapy update," *Epilepsy & Behavior*, vol. 88, pp. 2-10, Nov. 2018.
Wu, H. et al. "No enlargement of the right internal jugular vein of the dialysis patients in the Trendelenburg position," *Journal of the Chinese Medical Association*, vol. 76, pp. 401-406, Jul. 2013.
Yang, Y. et al. "The Present and Future of Vagus Nerve Stimulation," *Journal of Korean Neurosurgical Society*, 62(3), pp. 344-352, May 1, 2019.
Zangiabadi, N. et al. "Deep brain stimulation and drug-resistant epilepsy: a review of the literature," *Frontiers in Neurology*, vol. 10, p. 601, Jun. 6, 2019.
Zhou, J. et al. "Open-loop deep brain stimulation for the treatment of epilepsy: a systematic review of clinical outcomes over the past decade (2008-present)," *Neurosurgical Focus*, 45(2):E5, Aug. 2018.
Zijlmans, M. et al. "Heart rate changes and ECG abnormalities during epileptic seizures: prevalence and definition of an objective clinical sign," *Epilepsia*, vol. 43, pp. 847-854, Aug. 2002.

\* cited by examiner

METHODS, SYSTEMS, AND APPARATUS FOR CLOSED-LOOP NEUROMODULATION

CROSS-REFERENCE TO RELATED APPLICATIONS

This application is a divisional of U.S. patent application Ser. No. 17/659,381 filed on Apr. 15, 2022, now U.S. Pat. No. 11,672,986, which is a divisional of U.S. patent application Ser. No. 17/398,854 filed on Aug. 10, 2021, now U.S. Pat. No. 11,883,671, which is a continuation of International Patent Application No. PCT/US2020/059509 filed on Nov. 6, 2020, which claims the benefit of U.S. Provisional Application No. 62/932,906 filed on Nov. 8, 2019 and U.S. Provisional Application No. 63/062,633 filed on Aug. 7, 2020, the contents of which are incorporated herein by reference in their entireties.

TECHNICAL FIELD

This disclosure relates generally to endovascular neuromodulation and, more specifically, to methods, systems, and apparatus for closed-loop endovascular neuromodulation.

BACKGROUND

Vagal nerve stimulation has been successful at decreasing the frequency of seizures for people with medically refractory epilepsy and those whom resection is not a suitable option. Over 100,000 people have been implanted with a vagal nerve stimulation (VNS) system, although the outcome for such treatment is moderate. The responder rate, or the rate of patients who have their seizure frequencies reduced greater than 50%, is only 46.6%, with the median seizure reduction being 52.4%. In addition, there are potential side effects caused by the implantation of cuff-like electrodes directly around the vagal nerve, including injury and paralysis to the nerve and direct injury to the neck where surgical incisions are required to expose the nerve for electrode implantation.

Current VNS stimulation parameters are oftentimes open-loop, meaning that stimulation is administered continuously or according to a rigid schedule. Generally, stimulation is applied for around one to five minutes followed by a rest period for around four to ten minutes. Consequently, and due to the large amount of power being delivered, battery depletion is a concern as well as hardware malfunctions. Both require additional surgery for the removal of any implantable units for replacement of the battery or malfunctioning hardware components. Recent studies have also drawn attention to several potential side effects associated with this type of continuous or constant stimulation. See, e.g., Sun F T, Morrell M J, Wharen R E Jr., Responsive Cortical Stimulation for the Treatment of Epilepsy. *Neurotherapeutics*, 2008 Jan. 5 (1): 68-74 and Morrell M. Brain, Stimulation for Epilepsy: Can Scheduled or Responsive Neurostimulation Stop Seizures? *Current Opinion in Neurology*, 2006 April; 19 (2): 164-8.

Therefore, a solution is needed which addresses the above shortcomings and disadvantages of traditional neuromodulation systems. Such a solution should be safe, effective, and not overly difficult to implant.

SUMMARY

Systems, apparatus, and methods for treating medication refractory epilepsy are disclosed. In one embodiment, a method of treating epilepsy comprises detecting, using a first electrode array, an electrophysiological signal of a subject. The first electrode array can be coupled to a first endovascular carrier implanted within the subject. The method can also comprise analyzing the electrophysiological signal using a neuromodulation unit implanted within the subject and electrically coupled to the first electrode array and stimulating an intracorporeal target of the subject using a second electrode array in response to the electrophysiological signal detected. The second electrode array can be electrically coupled to the neuromodulation unit. The second electrode array can be coupled to a second endovascular carrier implanted within part of a bodily vessel superior to a base of a skull of the subject.

Stimulating the intracorporeal target can further comprise generating an electrical impulse using a pulse generator electrically coupled to the second electrode array. The pulse generator can be implanted within the subject. Generating the electrical impulse can further comprise increasing a current amplitude of the electrical impulse from 0 mA to up to 10 mA in 0.1 mA steps and increasing a voltage of the electrical impulse from 0 V to up to 10 V in 0.25 V steps. Moreover, the pulse width of the electrical impulse can be set at between 25 uS to about 600 μS. Furthermore, the frequency of the electrical impulse can be set at between 1 Hz and 400 Hz.

In some embodiments, the method can also comprise delivering the first endovascular carrier and the second endovascular carrier through a singular delivery catheter prior to detecting the electrophysiological signal of the subject. In other embodiments, the method can comprise delivering the first endovascular carrier through a first delivery catheter and delivering the second endovascular carrier through a second delivery catheter prior to detecting the electrophysiological signal of the subject. In further embodiments, the method can comprise delivering the first endovascular carrier through a first delivery catheter and delivering the second endovascular carrier through a second delivery catheter extending through the first delivery catheter.

In some embodiments, the method can further comprise stimulating the intracorporeal target of the subject using the first electrode array. In these embodiments, the method can also comprise using the second electrode array to detect or record the electrophysiological signal of the subject.

Also disclosed is an endovascular neuromodulation system for treating epilepsy and/or other conditions or disorders. The system can comprise a first electrode array configured to detect an electrophysiological signal of a subject. The first electrode array can be coupled to a first endovascular carrier configured to be implanted within the subject. The system can also comprise a second electrode array configured to stimulate an intracorporeal target of the subject. The second electrode array can be coupled to a second endovascular carrier configured to be implanted superior to a base of a skull of the subject. The system can further comprise an implantable neuromodulation unit electrically coupled to the first electrode array and the second electrode array.

The neuromodulation unit can be configured to analyze the electrophysiological signal detected by the first electrode array and generate an electrical impulse via a pulse generator to be transmitted to the second electrode array to stimulate the intracorporeal target in response to the electrophysiological signal detected.

The first endovascular carrier carrying the first electrode array can be implanted or configured to be implanted within a venous sinus of the subject. For example, the first endovascular carrier can be implanted or configured to be implanted within at least one of a superior sagittal sinus, an inferior sagittal sinus, a sigmoid sinus, a transverse sinus, and a straight sinus of the subject.

In some embodiments, the first endovascular carrier can be implanted or configured to be implanted within a superficial cerebral vein. For example, the first endovascular carrier can be implanted or configured to be implanted within at least one of a vein of Labbe, a vein of Trolard, a Sylvian vein, and a Rolandic vein.

In other embodiments, the first endovascular carrier can be implanted or configured to be implanted within a deep cerebral vein. For example, the first endovascular carrier can be implanted or configured to be implanted within at least one of a vein of Rosenthal, a vein of Galen, a superior thalamostriate vein, and an internal cerebral vein.

The first endovascular carrier can also be implanted within at least one of a central sulcal vein, a post-central sulcal vein, and a pre-central sulcal vein. In some embodiments, the first endovascular carrier can also be implanted or configured to be implanted within a vessel extending through a hippocampus or amygdala of the subject.

The intracorporeal target can be part of a vagus nerve of the subject. The second endovascular carrier can be implanted or configured to be implanted within part of an internal jugular vein superior to a jugular foramen of the subject. The second endovascular carrier can be implanted or configured to be implanted within a branch or tributary of the internal jugular vein. The second endovascular carrier can also be implanted within part of an internal carotid artery superior to the base of the skull of the subject.

In some embodiments, the intracorporeal target can be a cerebellum of the subject. In these embodiments and other embodiments, the second endovascular carrier can be implanted or configured to be implanted within at least one of a sigmoid sinus, a transverse sinus, and a straight sinus of the subject.

In other embodiments, the intracorporeal target can be a motor cortex of the subject. In these and other embodiments, the second endovascular carrier can be implanted or configured to be implanted within at least one of a superior sagittal sinus, an inferior sagittal sinus, a central sulcal vein, a post-central sulcal vein, and a pre-central sulcal vein.

The second endovascular carrier can be implanted or configured to be implanted within a superficial cerebral vein. For example, the second endovascular carrier can be implanted or configured to be implanted within at least one of a vein of Labbe, a vein of Trolard, a Sylvian vein, and a Rolandic vein.

The second endovascular carrier can also be implanted or configured to be implanted within a deep cerebral vein. For example, the second endovascular carrier can be implanted or configured to be implanted within at least one of a vein of Rosenthal, a vein of Galen, a superior thalamostriate vein, and an internal cerebral vein. In these and other embodiments, the intracorporeal target can be at least one of an anterior nucleus of thalamus, a centromedian nucleus of thalamus, a fornix, a hippocampus, a hypothalamus, a subthalamic nucleus, and a caudal zone incerta. In some embodiments, the second endovascular carrier can also be implanted or configured to be implanted within a vessel extending through a hippocampus or amygdala of the subject.

With respect to the implantation sites, the first endovascular carrier carrying the first electrode array and the second endovascular carrier carrying the second electrode array can be implanted in any combination of the bodily vessels disclosed herein. For example, the first endovascular carrier can be implanted within a venous sinus and the second endovascular carrier can be implanted within a superficial cerebral vein. Also, for example, the first endovascular carrier can be implanted within a deep cerebral vein and the second endovascular carrier can be implanted within an internal jugular vein.

The neuromodulation unit can be implanted or configured to be implanted within the subject. For example, the neuromodulation unit can be implanted or configured to be implanted within a forearm of the subject. Alternatively, the neuromodulation unit can be implanted or configured to be implanted within a pectoral region of the subject. The neuromodulation unit can also be implanted or configured to be implanted within an armpit region of the subject.

The first electrode array can be electrically coupled to the neuromodulation unit via a first transmission lead having a first lead diameter. The first transmission lead can extend through a neck of the subject. The first lead diameter can be between about 0.5 mm and 1.5 mm. The second electrode array can be electrically coupled to the neuromodulation unit via a second transmission lead having a second lead diameter. The second transmission lead can extend through a neck of the subject. The second lead diameter can be between about 0.5 mm and 1.5 mm. In other embodiments, the first electrode array and the second electrode array can be coupled to the neuromodulation unit via one transmission lead having a lead diameter. The one transmission lead can extend through a neck of the subject. In these embodiments, the lead diameter can be between about 0.5 mm and 1.5 mm.

In some embodiments, the pulse generator can be part of the neuromodulation unit. The pulse generator can be powered and activated by an extracorporeal device. For example, the pulse generator can comprise a first magnetic component and the extracorporeal device can comprise a second magnetic component configured to be magnetically coupled to the first magnetic component. The pulse generator can be configured to be charged by the extracorporeal device via electromagnetic induction when the extracorporeal device is placed in proximity to the pulse generator.

In these and other embodiments, the neuromodulation unit can be powered by one or more batteries. The extracorporeal device can be provided as part of an armband when the neuromodulation unit is implanted within an arm of the subject.

At least one of the first endovascular carrier and the second endovascular carrier can be an expandable stent or endovascular scaffold comprising an electrode array coupled to the expandable stent or endovascular scaffold. For example, at least one of the first endovascular carrier and the second endovascular carrier can be a self-expandable stent or self-expandable endovascular scaffold.

At least one of the first endovascular carrier and the second endovascular carrier can be a wire or cable configured to be wound or coiled comprising an electrode array coupled to the wire or cable. The wire or cable can be wound in a substantially helical pattern. In some embodiments, at least one of the first endovascular carrier and the second endovascular carrier can be a wire or cable comprising a sharp distal end for penetrating through lumen or vessel walls. Moreover, at least one of the first endovascular carrier and the second endovascular carrier can be a wire or cable comprising an anchor. For example, the anchor can be at least one of a barbed anchor and a radially-expandable anchor.

The neuromodulation unit can further comprise a telemetry unit. The telemetry unit can be configured to analyze the electrophysiological signal detected by comparing the electrophysiological signal against one or more signal thresholds or patterns. In some embodiments, the electrophysiological signal can be a local field potential (LFP) and/or an intracranial/cortical EEG measured within a brain of the subject. In these and other embodiments, the electrophysiological signal can be an electrocorticography signal.

The first endovascular carrier, the second endovascular carrier, and/or the transmission lead can be made in part of platinum tungsten, gold, aluminum, Nitinol wire, rhodium, iridium, nickel, nickel-chromium alloy, gold-palladium-rhodium alloy, chromium-nickel-molybdenum alloy, and/or stainless steel.

Also disclosed is another method of treating epilepsy. The method can comprise detecting, using a first electrode array, an electrophysiological signal of a subject. The first electrode array can be coupled to an endovascular carrier implanted superior to a base of a skull of the subject. The method can further comprise analyzing the electrophysiological signal using a neuromodulation unit electrically coupled to the first electrode array. The method can also comprise stimulating an intracorporeal target of the subject using a second electrode array in response to the electrophysiological signal detected. The second electrode array can be coupled to the same endovascular carrier.

Moreover, the electrodes of the second electrode array are separate from the electrodes of the first electrode array. In some embodiments, the first electrode array and the second electrode array can record or transmit data to the neuromodulation unit via different channels.

Stimulating the intracorporeal target can further comprise generating an electrical impulse using a pulse generator electrically coupled to the second electrode array. The pulse generator can be implanted within the subject. Stimulating the intracorporeal target further can comprise generating an electrical impulse using a pulse generator electrically coupled to the second electrode array. Generating the electrical impulse can further comprise increasing a current amplitude of the electrical impulse from 0 mA to up to 10 mA in 0.1 mA steps and increasing a voltage of the electrical impulse from 0 V to up to 10 V in 0.25 V steps. Moreover, the pulse width of the electrical impulse can be set at between 25 µS to about 600 µS. Furthermore, the frequency of the electrical impulse can be set at between 1 Hz and 400 Hz.

Also disclosed is another endovascular neuromodulation system for treating epilepsy and/or other conditions or disorders. The system can comprise a first electrode array configured to detect an electrophysiological signal of a subject. The first electrode array can be coupled to an endovascular carrier configured to be implanted endovascularly superior to the base of the skull of the subject. The system can also comprise a second electrode array configured to stimulate an intracorporeal target of the subject. The second electrode array can be coupled to the same endovascular carrier. The system can further comprise an implantable neuromodulation unit electrically coupled to the first electrode array and the second electrode array.

The neuromodulation unit can be configured to analyze the electrophysiological signal detected by the first electrode array and generate an electrical impulse via a pulse generator to be transmitted to the second electrode array to stimulate the intracorporeal target in response to the electrophysiological signal detected.

The intracorporeal target can be part of a vagus nerve of the subject. The endovascular carrier can be implanted or configured to be implanted within part of an internal jugular vein superior to a jugular foramen of the subject. In some embodiments, the endovascular carrier can be implanted or configured to be implanted within a branch or tributary of the internal jugular vein. The endovascular carrier can be implanted or configured to be implanted within part of an internal carotid artery superior to the base of the skull of the subject.

In some embodiments, the intracorporeal target can be a cerebellum of the subject. In these embodiments, the endovascular carrier can be implanted or configured to be implanted within at least one of a sigmoid sinus, a transverse sinus, and a straight sinus of the subject.

In other embodiments, the intracorporeal target can be a motor cortex of the subject. In these embodiments, the endovascular carrier can be implanted or configured to be implanted within at least one of a superior sagittal sinus, an inferior sagittal sinus, a central sulcal vein, a post-central sulcal vein, and a pre-central sulcal vein.

The endovascular carrier can also be implanted within a superficial cerebral vein. For example, the endovascular carrier can be implanted or configured to be implanted within at least one of a vein of Labbe, a vein of Trolard, a Sylvian vein, and a Rolandic vein.

The endovascular carrier can be implanted or configured to be implanted within a deep cerebral vein. For example, the endovascular carrier can be implanted or configured to be implanted within at least one of a vein of Rosenthal, a vein of Galen, a superior thalamostriate vein, and an internal cerebral vein.

The neuromodulation unit can be implanted or configured to be implanted within the subject. For example, the neuromodulation unit can be implanted or configured to be implanted within a forearm of the subject. Alternatively, the neuromodulation unit can be implanted or configured to be implanted within a pectoral region of the subject. The neuromodulation unit can also be implanted or configured to be implanted within an armpit region of the subject.

The first electrode array can be electrically coupled to the neuromodulation unit via a first transmission lead having a first lead diameter. The first transmission lead can extend through a neck of the subject. The first lead diameter can be between about 0.5 mm and 1.5 mm. The second electrode array can be electrically coupled to the neuromodulation unit via a second transmission lead having a second lead diameter. The second transmission lead can extend through a neck of the subject. The second lead diameter can be between about 0.5 mm and 1.5 mm.

In other embodiments, the first electrode array and the second electrode array can be coupled to the neuromodulation unit via one transmission lead having a lead diameter. The one transmission lead can extend through a neck of the subject. In these embodiments, the lead diameter can be between about 0.5 mm and 1.5 mm.

In some embodiments, the pulse generator can be part of the neuromodulation unit. The pulse generator can be powered and activated by an extracorporeal device. For example, the pulse generator can comprise a first magnetic component and the extracorporeal device can comprise a second magnetic component configured to be magnetically coupled to the first magnetic component. The pulse generator can be configured to be charged by the extracorporeal device via electromagnetic induction when the extracorporeal device is placed in proximity to the pulse generator.

In these and other embodiments, the neuromodulation unit can be powered by one or more batteries. The extracorporeal device can be provided as part of an armband when the neuromodulation unit is implanted within an arm of the subject.

In some embodiments, the endovascular carrier can be an expandable stent or endovascular scaffold comprising an electrode array coupled to the expandable stent or endovascular scaffold. For example, the endovascular carrier can be a self-expandable stent or self-expandable endovascular scaffold.

In other embodiments, the endovascular carrier can be a wire or cable configured to be wound or coiled comprising an electrode array coupled to the wire or cable. The wire or cable can be wound in a substantially helical pattern.

In some embodiments, the endovascular carrier can be a wire or cable comprising a sharp distal end for penetrating through lumen or vessel walls. Moreover, the endovascular carrier can be a wire or cable comprising an anchor. For example, the anchor can be at least one of a barbed anchor and a radially-expandable anchor.

The neuromodulation unit can further comprise a telemetry unit. The telemetry unit can be configured to analyze the electrophysiological signal detected by comparing the electrophysiological signal against one or more signal thresholds or patterns. In some embodiments, the electrophysiological signal can be a local field potential (LFP) and/or an intracranial/cortical EEG measured within a brain of the subject. In these and other embodiments, the electrophysiological signal can be an electrocorticography signal.

The endovascular carrier and/or the transmission lead(s) can be made in part of platinum tungsten, gold, aluminum, Nitinol wire, rhodium, iridium, nickel, nickel-chromium alloy, gold-palladium-rhodium alloy, chromium-nickel-molybdenum alloy, and/or stainless steel.

BRIEF DESCRIPTION OF THE DRAWINGS

The drawings shown and described are exemplary embodiments and non-limiting. Like reference numerals indicate identical or functionally equivalent features throughout.

DETAILED DESCRIPTION

Figure 1:
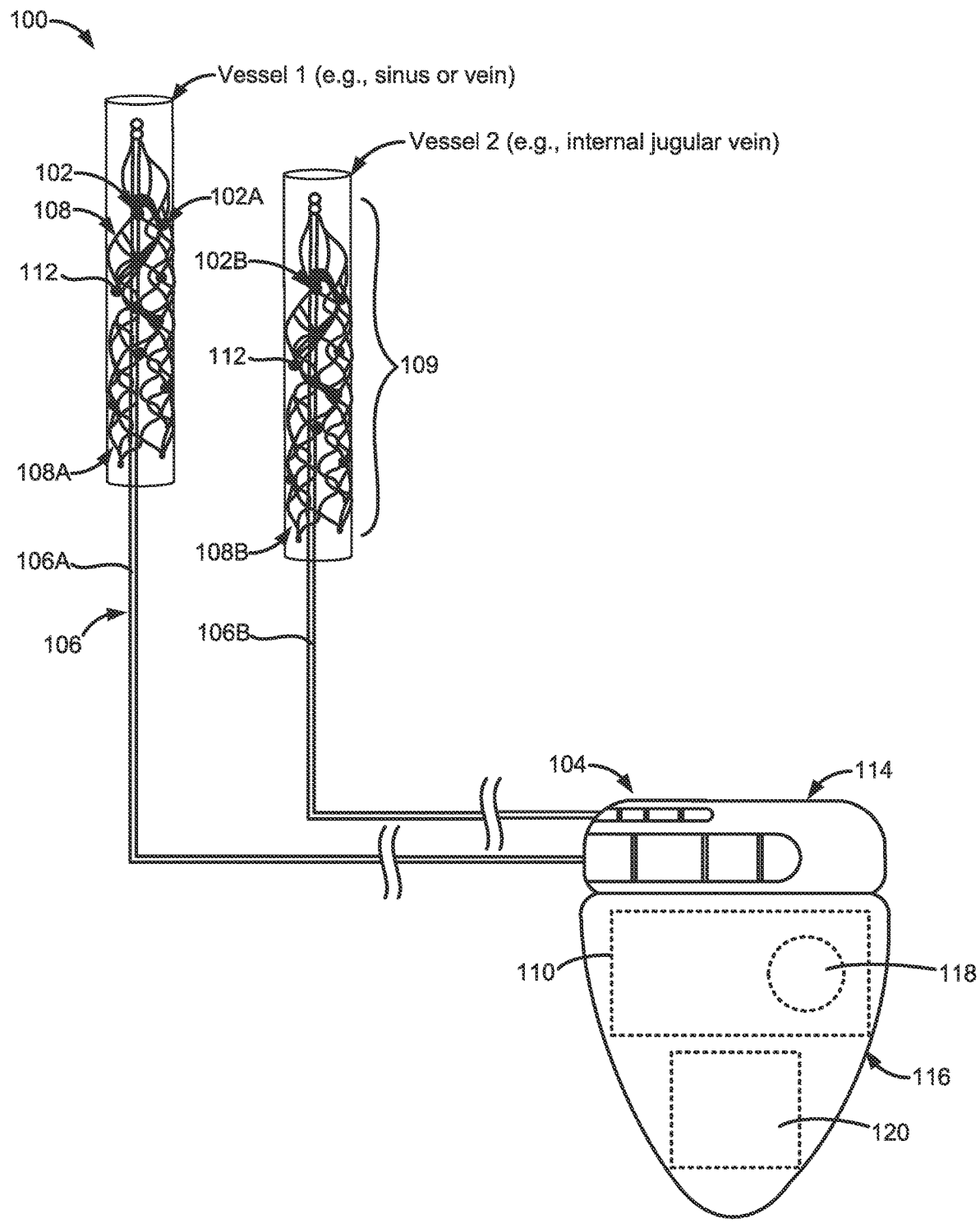
FIG. 1 illustrates one embodiment of an endovascular neuromodulation system for treating epilepsy and other disorders/conditions.

FIG. 1 illustrates one embodiment of an endovascular neuromodulation system 100 for treating epilepsy and other disorders/conditions. The neuromodulation system 100 can comprise a plurality of electrode arrays 102 electrically coupled to a neuromodulation unit 104 via transmission leads 106 or wires. For example, the neuromodulation system 100 can comprise a first electrode array 102A and a second electrode array 102B electrically coupled to the neuromodulation unit 104.

Each of the electrode arrays 102 can be coupled to an endovascular carrier 108. For example, the first electrode array 102A can be coupled to a first endovascular carrier 108A configured to be implanted endovascularly within the subject. The second electrode array 102B can be coupled to a second endovascular carrier 108B configured to be implanted endovascularly within the subject.

In some embodiments, the first endovascular carrier 108A and the second endovascular carrier 108B can be implanted within different vessels (e.g., different veins, arteries, or sinuses) of the subject. In other embodiments, the first endovascular carrier 108A and the second endovascular carrier 108B can be implanted within the same vessel or within different segments of the same vessel.

In certain embodiments, the first electrode array 102A can be configured to detect or record an electrophysiological signal of a subject and the second electrode array 102B can be configured to stimulate an intracorporeal target (e.g., a target nerve, a target brain region or area, or other target tissue) of the subject. In these embodiments, the neuromodulation unit 104 can be configured to analyze the electrophysiological signal detected or recorded by the first electrode array 102A and transmit an electrical impulse to the second electrode array 102B via a pulse generator 110 in response to the electrophysiological signal detected or recorded.

In other embodiments, the first electrode array 102A and the second electrode array 102B can both be configured to detect or record an electrophysiological signal of the subject. In additional embodiments, the first electrode array 102A and the second electrode array 102B can both be configured to stimulate one or more intracorporeal targets of the subject. The intracorporeal target(s) will be discussed in more detail in later sections.

The first electrode array 102A can comprise a plurality of electrodes 112 coupled to the first endovascular carrier 108A. For example, the first electrode array 102A can comprise between 2 and 16 electrodes. In other embodiments, the first electrode array 102A can comprise between 16 and 20 electrodes or more than 20 electrodes.

The second electrode array 102B can comprise a plurality of electrodes 112 coupled to the second endovascular carrier 108B. For example, the second electrode array 102B can comprise between 2 and 16 electrodes. In other embodiments, the second electrode array 102B can comprise between 16 and 20 electrodes or more than 20 electrodes.

When the electrode arrays 102 (e.g., any of the first electrode array 102A or the second electrode array 102B) are used to detect or record an electrophysiological signal of the subject, the electrode arrays can be referred to as recording electrode arrays. Moreover, when the electrode arrays (e.g., any of the first electrode array 102A or the second electrode array 102B) are used to stimulate an intracorporeal target of the subject, the electrode arrays can be referred to as stimulating electrode arrays.

In some embodiments (for example, the embodiment shown in FIG. 1), the first endovascular carrier 108A and the second endovascular carrier 108B can be expandable stents or endovascular scaffolds. The endovascular carrier and the electrode arrays coupled to such a carrier can be referred to as a stent-electrode array 109. Stent-electrode arrays 109 will be discussed in more detail in later sections.

In other embodiments, at least one of the first endovascular carrier 108A and the second endovascular carrier 108B can be a biocompatible coiled wire 200 (see, e.g., FIG. 2A), a biocompatible anchored wire 208 (see, e.g., FIG. 2C), or a combination thereof.

In certain embodiments, the first endovascular carrier 108A can be the same as the second endovascular carrier 108B (e.g., both the first endovascular carrier 108A and the second endovascular carrier 108B can be stent-electrode arrays 109, coiled wires 200, or anchored wires 208). In other embodiments, the first endovascular carrier 108A can be different from the second endovascular carrier 108B (e.g., the first endovascular carrier 108A can be a stent-electrode array 109 and the second endovascular carrier 108B can be a coiled wire 200).

Although FIG. 1 illustrates the neuromodulation system 100 comprising two electrode arrays 102 and two endovascular carriers 108, it is contemplated by this disclosure that the neuromodulation system 100 can comprise between three to five electrode arrays 102 and endovascular carriers 108. In additional embodiments, the neuromodulation system 100 can comprise between five to ten electrode arrays 102 and endovascular carriers 108.

The neuromodulation unit 104 can be configured to be implanted within the subject. In some embodiments, the neuromodulation unit 104 can be configured to be implanted within a forearm of the subject (see, e.g., FIG. 3B). In other embodiments, the neuromodulation unit 104 can be configured to be implanted within a pectoral region of the subject (see, e.g., FIG. 3A). The neuromodulation unit 104 can also be implanted or configured to be implanted within an armpit region of the subject.

Each of the first electrode array 102A and the second electrode array 102B can be coupled via one or more transmission leads 106 or lead wires to the neuromodulation unit 104. In some embodiments, the transmission leads 106 can be inserted or otherwise coupled to a header portion 114 of the neuromodulation unit 104.

The header portion 114 can comprise a different plug receptor for leads or plugs coming from different electrode arrays. For example, the header portion 114 can comprise a 0.9 mm plug receptor for receiving a plug or connector from a first transmission lead 106A connected or coupled to the first electrode array 102A serving as the recording electrode array and a 1.3 mm plug receptor for receiving a plug or connector from a second transmission lead 106B connected or coupled to the second electrode array 102B serving as the stimulation electrode array.

The neuromodulation unit 104 can comprise a unit housing 116. The unit housing 116 can be a hermetically sealed housing or casing such that electronic components within the neuromodulation unit 104 are encapsulated by the unit housing 116. The unit housing 116 can be made of a biocompatible material. For example, the unit housing 116 can be made in part of a metallic material (e.g., titanium, stainless steel, platinum, or a combination thereof), a polymeric material, or a combination thereof.

In some embodiments, the pulse generator 110 can be part of the neuromodulation unit 104 or contained within the unit housing 116. In some embodiments, the implantable neuromodulation unit 104 can comprise one or more batteries (e.g., rechargeable or non-rechargeable batteries). In certain embodiments, the batteries of the neuromodulation unit 104 can be recharged via wireless inductive charging.

Figure 3A:
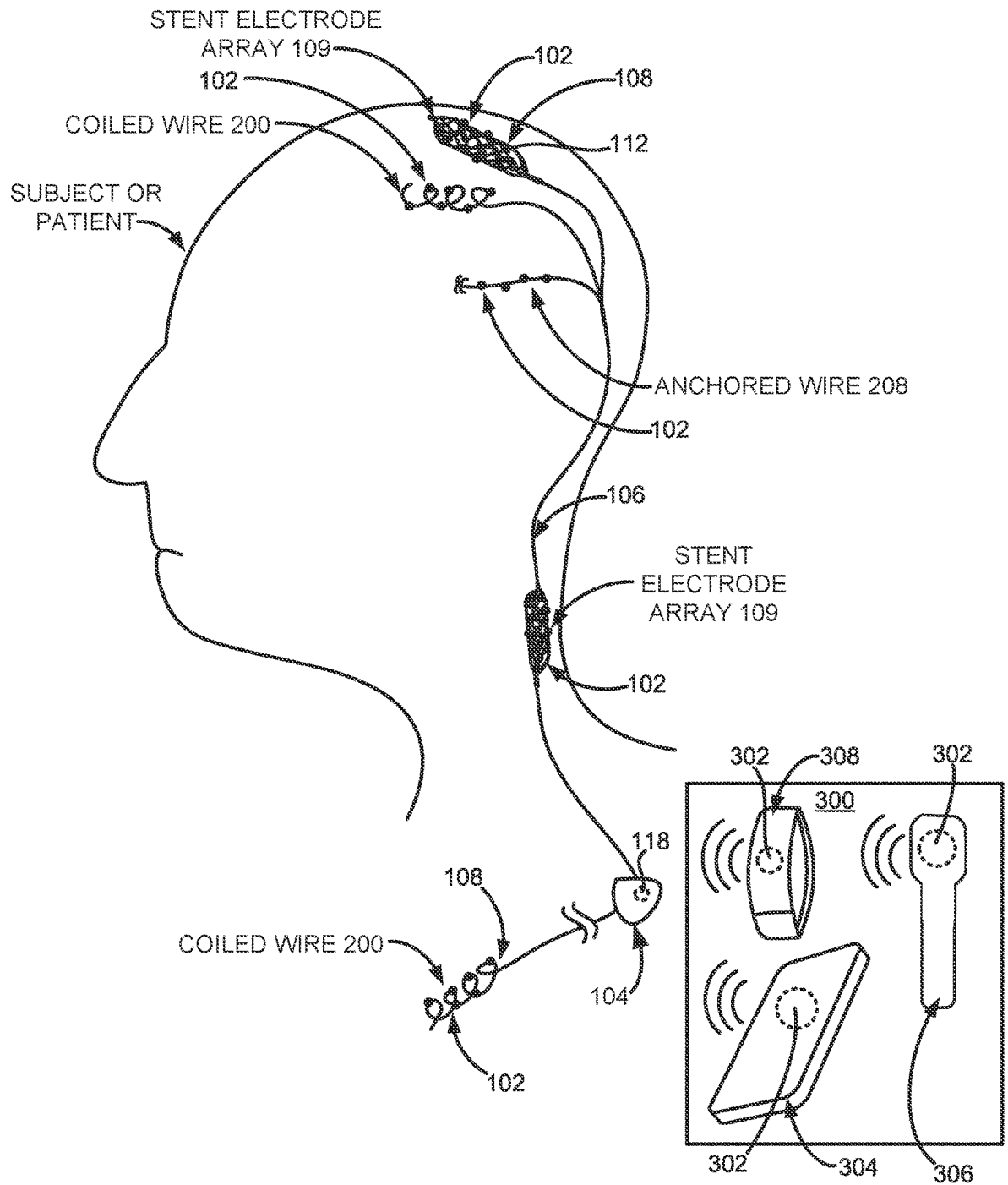
FIG. 3A illustrates possible implantation sites for components of the neuromodulation system.

In other embodiments, the neuromodulation unit 104 can be powered and/or activated by an extracorporeal device 300 (see, for example, FIG. 3A). The neuromodulation unit 104 can comprise a first magnetic component 118 and the extracorporeal device 300 can comprise a second magnetic component 302 (see, for example, FIG. 3A) configured to be magnetically coupled to the first magnetic component 118. The neuromodulation unit 104, including the pulse generator 110, can be configured to be charged by the extracorporeal device 300 via electromagnetic induction or activated by the extracorporeal device 300 when the extracorporeal device 300 is placed in proximity to the neuromodulation unit 104, such as by holding the extracorporeal device 300 close to an implantation site of the neuromodulation unit 104. In these embodiments where the neuromodulation unit 104 and the pulse generator 110 are the same device, any reference to the neuromodulation unit 104 can also refer to the pulse generator 110.

In other embodiments, the pulse generator 110 can be a separate device or apparatus from the neuromodulation unit 104. In these embodiments, the pulse generator 110 can be implanted within the subject and the neuromodulation unit 104 can be an extracorporeal unit located and operating outside of the body of the subject. In these embodiments, the neuromodulation unit 104 can serve as the extracorporeal device 300 and can process data received wirelessly or via physical leads from the first electrode array 102A, the second electrode array 102B, or a combination thereof.

In further embodiments, the implantable pulse generator 110 can comprise one or more batteries (e.g., rechargeable or non-rechargeable batteries). In certain embodiments, the batteries of the pulse generator 110 can be recharged via wireless inductive charging.

When the pulse generator 110 is a separate device implanted within the subject (e.g., implanted within the forearm, the pectoral region, the armpit region, etc.), the pulse generator 110 can be powered and activated by the extracorporeal device 300 (scc, e.g., FIG. 3A). In some embodiments, the pulse generator 110 can comprise a first magnetic component 118 and the extracorporeal device 300 can comprise a second magnetic component 302 configured to be magnetically coupled to the first magnetic component 118. The pulse generator 110 can be configured to be charged by the extracorporeal device 300 via electromagnetic induction when the extracorporeal device 300 is placed in proximity to the pulse generator 110, such as by holding the extracorporeal device 300 close to an implantation site of the pulse generator 110.

The neuromodulation unit 104 can further comprise a telemetry unit 120 or telemetry module (e.g., a telemetry hardware module, a telemetry software module, or a combination thereof). The telemetry unit 120 can be configured to analyze the electrophysiological signal detected or recorded by an electrode array by comparing the electrophysiological signal against one or more predetermined signal thresholds or patterns. For example, the neuromodulation unit 104 (or the telemetry unit 120 within the neuromodulation unit 104) can comprise one or more processors and one or more memory units. The one or more processors can be programmed to execute instructions stored in the one or more memory units to compare the electrophysiological signal against one or more predetermined signal thresholds or patterns as part of the analysis.

In some embodiments, the electrophysiological signal can be a local field potential (LFP) and/or an intracranial/cortical EEG measured within a brain of the subject using any of the electrode arrays (e.g., the first electrode array 102A, the second electrode array 102B, or a combination thereof) implanted endovascularly within the subject. In other embodiments, the electrophysiological signal can be an intracranial or cortical electroencephalography (EEG) signal.

In other embodiments, the electrophysiological signal can be an electrocorticography (ECoG) signal received by the telemetry unit 120 from an ECoG electrode array deployed on a surface of the brain. For example, the ECoG electrode array can be a flexible or stretchable electrode-mesh or one or more electrode patches placed on a surface of the brain.

In further embodiments, the electrophysiological signal can be a signal indicating a heart rate or change in heart rate of the subject. For example, the electrophysiological signal can be an electrocardiogram (ECG/EKG) signal measured by the neuromodulation unit 104 when the neuromodulation unit 104 is implanted within a pectoral region or implanted within a subclavian space of the subject.

In certain embodiments, the electrophysiological signal can be an EEG signal received by the telemetry unit 120 from a plurality of external electrodes (an external electrode array) placed on a scalp of the subject. For example, the EEG signal can be obtained from a head-mounted EEG monitoring system (e.g., EEG skull cap or EEG-visor). In these embodiments, the EEG electrodes can serve as the recording or detecting electrode array.

The electrophysiological signal can provide information or data that can be used to predict or indicate whether the subject is about to experience an epileptic seizure. For example, when the electrophysiological signal is an EEG signal, the neuromodulation unit 104 can command the pulse generator 110 to generate an electrical impulse when epileptiform transients or other seizure pre-onset signatures are detected in the EEG signal.

The neuromodulation unit 104 (or the telemetry unit 120) can adjust or vary one or more signal thresholds. Moreover, the neuromodulation unit 104 can also select from different signal thresholds. For example, the neuromodulation unit 104 can raise or lower a signal threshold based on how often the subject experiences a seizure after a signal threshold is met (or not met).

The neuromodulation system 100 can be considered to operate in a closed-loop mode or to provide "responsive neurostimulation" when the intracorporeal target is stimulated in response to a detected electrophysiological signal associated or correlated with the onset of epileptic seizures. In some embodiments, the system 100 can also classify or stratify the electrophysiological signals detected or recorded into low risk, medium risk, or high risk and only generate the electrical impulse when the signal is considered medium risk or high risk.

The neuromodulation unit 104 can be configured to analyze the electrophysiological signal detected or recorded by at least one of the electrode arrays (e.g., any of the first electrode array 102A, the second electrode array 102B, or a combination thereof) and transmit an electrical impulse to the same electrode array or another electrode array via the pulse generator 110 in response to the electrophysiological signal detected or recorded.

The electrical impulse can be biphasic, monophasic, sinusoidal, or a combination thereof. The pulse generator 110 can generate the electrical impulse by increasing a current amplitude of the electrical impulse from 0 mA to up to 10 mA in 0.1 mA steps and increasing a voltage of the electrical impulse from 0 V to up to 10 V in 0.25 V steps. The electrical impulse generated can have a pulse width of between 25 µS to about 600 µS. A timing parameter of the electrical impulse can also be adjusted to allow for different stimulation timing patterns.

The electrical impulse generated can have a frequency between 1 Hz and 400 Hz. For example, a frequency of the electrical impulse can be set at a low frequency (between about 1 Hz to 10 Hz), a medium frequency (between about 10 Hz to 150 Hz), and a high frequency (between about 150 Hz to 400 Hz). Stimulating the intracorporeal target (e.g., the vagus nerve) can increase blood flow to key areas of the brain and raise levels of certain neurotransmitters involved in suppressing seizure activity (e.g., inhibitory neurotransmitters such as gamma-aminobutyric acid (GABA)).

In other embodiments, the neuromodulation system 100 can operate in an open-loop mode or configuration such that the intracorporeal target is stimulated via an electrode array intermittently or periodically based on a pre-set schedule.

FIGS. 2A-2D illustrates various other embodiments of endovascular carriers 108 that can be used to carry an electrode array 102 and secure the electrode array 102 to an implantation site within a vasculature of the subject.

As previously shown in FIG. 1, the endovascular carrier 108 can be an expandable stent or endovascular scaffold comprising an electrode array 102 coupled to the expandable stent or endovascular scaffold. The expandable stent or endovascular scaffold can comprise multiple filaments woven into a tubular-like structure.

In some embodiments, the stent or scaffold is configured to be self-expandable. For example, the stent or scaffold can self-expand from a collapsed or crimped configuration to an expanded configuration when deployed within a vasculature of the subject. For example, the stent or scaffold can self-expand into a shape or diameter pre-set to fit a particular vein, artery, or another vessel. In other embodiments, the stent or scaffold can be expanded by a balloon catheter.

The electrodes 112 of the electrode array 102 can be affixed, secured, or otherwise coupled to an external boundary or radially outward portion of the expandable stent or scaffold. For example, the electrodes 112 of the electrode array 102 can be arranged along filaments making up the external boundary or radially outward portion of the expandable stent or scaffold (i.e., the part of the stent or scaffold configured to be in contact with the vessel lumen).

In some embodiments, the filaments of the expandable stent or endovascular scaffold can be made in part of a shape-memory alloy. For example, the filaments of the expandable stent or endovascular scaffold can be made in part of Nitinol (e.g., Nitinol wire). The filaments of the expandable stent or endovascular scaffold can also be made in part of stainless steel, gold, platinum, nickel, titanium, tungsten, aluminum, nickel-chromium alloy, gold-palladium-rhodium alloy, chromium-nickel-molybdenum alloy, iridium, rhodium, or a combination thereof. The filaments of the expandable stent or endovascular scaffold can also be made in part of a shape memory polymer.

When the endovascular carrier 108 is an expandable stent or endovascular scaffold carrying an electrode array 102, the entire carrier and array assembly can be referred to as a stent-electrode array 109.

The stent-electrode arrays 109 disclosed herein can be any of the stents, scaffolds, stent-electrodes, or stent-electrode arrays disclosed in U.S. Patent Pub. No. US 2020/0363869; U.S. Patent Pub. No. 2020/0078195; U.S. Patent Pub. No. 2020/0016396; U.S. Patent Pub. No. 2019/0336748; U.S. Patent Pub. No. US 2014/0288667; U.S. Pat. Nos. 10,575,783; 10,485,968; 10,729,530, 10,512,555; U.S. Pat. App. No. 62/927,574 filed on Oct. 29, 2019; U.S. Pat. App. No. 62/932,906 filed on Nov. 8, 2019; U.S. Pat. App. No. 62/932,935 filed on Nov. 8, 2019; U.S. Pat. App. No. 62/935,901 filed on Nov. 15, 2019; U.S. Pat. App. No. 62/941,317 filed on Nov. 27, 2019; U.S. Pat. App. No. 62/950,629 filed on Dec. 19, 2019; U.S. Pat. App. No. 63/003,480 filed on Apr. 1, 2020; U.S. Pat. App. No. 63/057,379 filed on Jul. 28, 2020, the contents of which are incorporated herein by reference in their entireties.

Figure 2A:
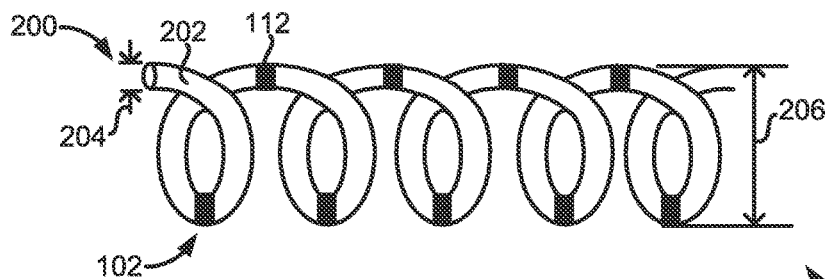
FIGS. 2A-2D illustrate various embodiments of endovascular carriers.

FIG. 2A illustrates another embodiment of the endovascular carrier 108 as a coiled wire 200. The coiled wire 200 can be used in vessels that are too small to accommodate the stent-electrode array 109.

The coiled wire 200 can be a biocompatible wire 202 or microwire configured to wind itself into a coiled pattern or a substantially helical pattern. The electrodes 112 of the electrode array 102 can be arranged such that the electrodes 112 are scattered along a length of the coiled wire 200. More specifically, the electrodes 112 of the electrode array 102 can be affixed, secured, or otherwise coupled to distinct points along a length of the coiled wire 200. The electrodes 112 of the electrode array 102 can be separated from one another such that no two electrodes 112 are within a predetermined separation distance (e.g., at least 10 µm, at least 100 µm, or at least 1.0 mm) from one another.

In some embodiments, the wire 202 or microwire can be configured to automatically wind itself into a coiled configuration (e.g., helical pattern) when the wire 202 or microwire is deployed out of a delivery catheter. For example, the coiled wire 200 can automatically attain its coiled configuration via shape memory when the delivery catheter or sheath is retracted. The coiled configuration or shape can be a preset or shape memory shape of the wire 202 or microwire prior to the wire 202 or microwire being introduced into a delivery catheter. The preset or pre-trained shape can be made to be larger than the diameter of the anticipated deployment or implantation vessel to enable the radial force exerted by the coils to secure or position the coiled wire 200 in place within the deployment or implantation vessel.

In other embodiments, the coiled wire 200 can attain the coiled configuration when a pushing force is applied to the wire 202 or microwire to compel or otherwise bias the wire 202 or microwire into the coiled configuration.

As shown in FIG. 2A, the coiled wire 200 can have a wire diameter 204 and a coil diameter 206. The wire diameter 204 can be a diameter of the underlying wire 202 or microwire used to form the endovascular carrier 108. In some embodiments, the wire diameter 204 can be between about 25 µm to about 1.0 mm. In other embodiments, the wire diameter 204 can be between about 100 µm to about 500 µm.

The coil diameter 206 can be between 1.0 mm to 15.0 mm. More specifically, the coil diameter 206 can be between about 3.0 mm to about 8.0 mm (e.g., about 6.0 mm or 7.0 mm). In some embodiments, the coil diameter 206 can be between 15.0 mm to about 25.0 mm. The coil diameter 206 can be set based on a diameter of a target vessel or deployment vessel.

The wire 202 or microwire can be made in part of a shape-memory alloy, a shape memory polymer, or a combination thereof. For example, wire 202 or microwire can be made in part of Nitinol (e.g., Nitinol wire). The wire 202 or microwire can also be made in part of stainless steel, gold, platinum, nickel, titanium, tungsten, aluminum, nickel-chromium alloy, gold-palladium-rhodium alloy, chromium-nickel-molybdenum alloy, iridium, rhodium, or a combination thereof.

Figure 2B:
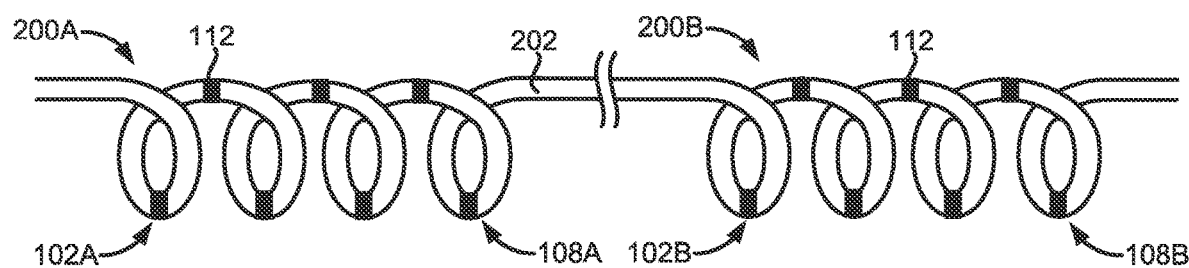

FIG. 2B illustrates that a first electrode array 102A can be carried by a first coiled wire 200A and a second electrode array 102B can be carried by a second coiled wire 200B connected to the first coiled wire 200A. In this embodiment, the first coiled wire 200A can serve as the first endovascular carrier 108A and the second coiled wire 200B can serve as the second endovascular carrier 108B. Each of the first coiled wire 200A and the second coiled wire 200B can be the same as the coiled wire 200 (see FIG. 2A) previously discussed.

The first coiled wire 200A can be connected to the second coiled wire 200B by an uncoiled segment of the wire 202 or microwire. For example, the first coiled wire 200A can be connected to the second coiled wire 200B by an uncoiled segment of the same wire 202 or microwire used to make the first coiled wire 200A and the second coiled wire 200B.

As will be discussed in more detail in later sections, the first coiled wire 200A serving as the first endovascular carrier 108A and the second coiled wire 200B serving as the second endovascular carrier 108B can be implanted along different segments of the same vessel or implanted within different vessels.

In some embodiments, the first electrode array 102A carried by the first coiled wire 200A can serve as a recording electrode array and the second electrode array 102B carried by the second coiled wire 200B can serve as the stimulating electrode array. In other embodiments, both the first electrode array 102A carried by the first coiled wire 200A and the second electrode array 102B carried by the second coiled wire 200B can serve as the recording electrode arrays and/or the stimulating electrode arrays.

Figure 2C:
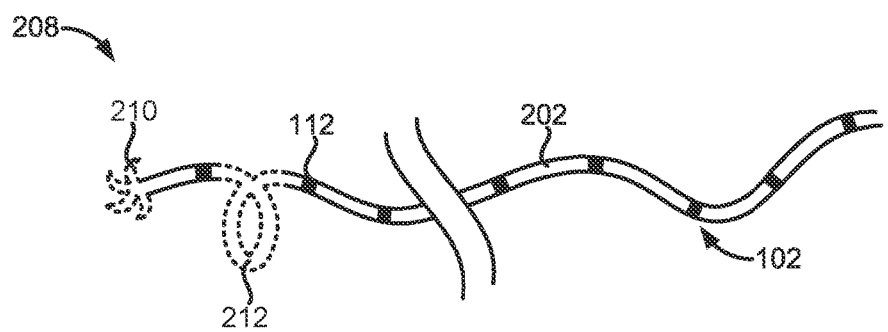

FIG. 2C illustrates a further embodiment of the endovascular carrier 108 as an anchored wire 208. The anchored wire 208 can be used in vessels that are too small or too tortuous to accommodate either the coiled wire 200 or the stent-electrode array 109.

The anchored wire 208 can comprise a biocompatible wire 202 or microwire attached or otherwise coupled to an anchor or another type of endovascular securement mechanism.

FIG. 2C illustrates that the anchored wire 208 can comprise a barbed anchor 210, a radially-expandable anchor 212, or a combination thereof (both the barbed anchor 210 and the radially-expandable anchor 212 are shown in broken or phantom lines in FIG. 2C).

In some embodiments, the barbed anchor 210 can be positioned at a distal end of the anchored wire 208. In other embodiments, the barbed anchor 210 can be positioned along one or more sides of the wire 202 or microwire. The barbs of the barbed anchor 210 can secure or moor the anchored wire 208 to an implantation site within the subject.

The radially-expandable anchor 212 can be a segment of the wire 202 or microwire shaped as a coil or loop. The coil or loop can be sized to allow the coil or loop to conform to a vessel lumen and to expand against a lumen wall to secure the anchored wire 208 to an implantation site within the vessel. For example, the coil or loop can be sized to be larger than the diameter of the anticipated deployment or implantation vessel to enable the radial force exerted by the coil or loop to secure or position the anchored wire 208 in place within the deployment or implantation vessel.

In some embodiments, the radially-expandable anchor 212 can be positioned at a distal end of the anchored wire 208. In other embodiments, the radially-expandable anchor 212 can be positioned along a segment of the anchored wire 208 proximal to the distal end.

The electrodes 112 of the electrode array 102 can be scattered along a length of the coiled wire 200. More specifically, the electrodes 112 of the electrode array 102 can be affixed, secured, or otherwise coupled to distinct points along a length of the anchored wire 208. The electrodes 112 of the electrode array 102 can be separated from one another such that no two electrodes 112 are within a predetermined separation distance (e.g., at least 10 μm, at least 100 μm, or at least 1.0 mm) from one another.

Although FIG. 2C illustrates the anchored wire 208 having only one barbed anchor 210 and one radially-expandable anchor 212, it is contemplated by this disclosure that the anchored wire 208 can comprise a plurality of barbed anchors 210 and/or radially-expandable anchors 212.

Figure 2D:
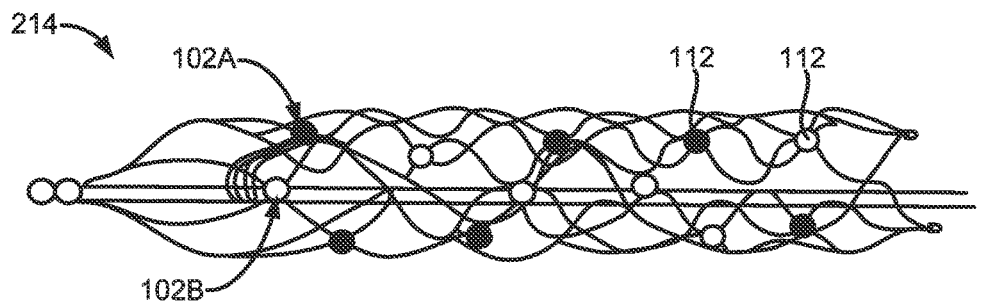

FIG. 2D illustrates an embodiment of an endovascular carrier 214 carrying different electrode arrays 102 (e.g., the first electrode array 102A and the second electrode array 102B). As shown in FIG. 2D, the endovascular carrier 214 can be the stent-electrode array 109 previously discussed.

In this embodiment, two electrode arrays 102 can be coupled to the same expandable stent or endovascular scaffold. In other embodiments, three or more electrode arrays 102 can be coupled to the same expandable stent or endovascular scaffold.

Although FIG. 2D illustrates the electrodes 112 of the first electrode array 102A using dark circles and the electrodes 112 of the second electrode array 102B using white circles, it should be understood by one of ordinary skill in the art that the difference in color is only for ease of illustration.

The electrodes 112 of the first electrode array 102A can be used as dedicated recording or detection electrodes and the electrodes 112 of the second electrode array 102B can be used as dedicated stimulating electrodes. In this manner, only one endovascular carrier is needed to deploy both the recording electrode array and the stimulating electrode array. Moreover, in this embodiment, the electrodes 112 of the first electrode array 102A can record and communicate via different data or communication channels than electrodes 112 of the second electrode array 102B.

Although FIG. 2D illustrates the endovascular carrier 214 as an expandable stent or scaffold, it is contemplated by this disclosure that any of endovascular carriers disclosed herein, including the coiled wire 200 and the anchored wire 208, can be used as an endovascular carrier for carrying the at least two types of electrode arrays 102.

The electrodes 112 of the electrode arrays 102 depicted in FIGS. 2A-2D can be made in part of platinum, platinum black, another noble metal, or alloys or composites thereof. For example, the electrodes 112 of the electrode arrays 102 can be made of gold, iridium, palladium, a gold-palladium-rhodium alloy, rhodium, or a combination thereof. In some embodiments, the electrodes 112 can be made of a metallic composite with a high charge injection capacity (e.g., a platinum-iridium alloy or composite).

In some embodiments, the electrodes 112 can be shaped as circular disks having a disk diameter of between about 100 μm to 1.0 mm. In other embodiments, the electrodes 112 can have a disk diameter of between 1.0 mm and 1.5 mm. In additional embodiments, the electrodes 112 can be cylindrical, spherical, cuff-shaped, ring-shaped, partially ring-shaped (e.g., C-shaped), or semi-cylindrical, The electrodes 112 can have their conductive properties enhanced by increasing the surface area of the electrodes 112 through surface roughening with chemical or electrochemical roughening methods or coating with a conductive polymeric coating such as poly (3,4-cthylenedioxythiophene) polystyrene sulfonate (PEDOT: PSS).

FIG. 3A illustrates that the neuromodulation unit 104 and the endovascular carriers 108 carrying the electrode arrays 102 can be implanted within the subject. In some embodiments, the neuromodulation unit 104 can be powered by a portable power supply such as one or more rechargeable batteries. In these and other embodiments, the batteries of the neuromodulation unit 104 can be recharged by an extracorporeal device 300 via electromagnetic induction. In some embodiments, the neuromodulation unit 104 can also be activated or powered by the extracorporeal device 300 when the extracorporeal device 300 is placed in proximity to the neuromodulation unit 104 (e.g., when held up next to the implantation site of the neuromodulation unit 104).

For example, the neuromodulation unit 104 can comprise a first magnetic component 118 (e.g., a receiving or secondary coil) and the extracorporeal device 300 can comprise a second magnetic component 302 (e.g., a primary or transmission coil) configured to be magnetically coupled to the first magnetic component 118. The extracorporeal device 300 can charge or power the neuromodulation unit 104 via electromagnetic induction.

In some embodiments, the pulse generator 110 can be a standalone device separate from the neuromodulation unit 104. In these embodiments, the pulse generator 110 can also comprise a first magnetic component 118 (e.g., a receiving or secondary coil) configured to be magnetically coupled to a second magnetic component 302 (e.g., a primary or transmission coil) within the extracorporeal device 300. In these embodiments, the pulse generator 110 can be charged or powered by the extracorporeal device 300 via electromagnetic induction.

As shown in FIG. 3A, any of the endovascular carriers 108 can be implanted within a cortical or cerebral vessel of the subject. For example, an electrode array 102 coupled to a stent-electrode array 109 serving as the endovascular carrier 108 can be implanted within a venous sinus (e.g., a superior sagittal sinus) of the subject. The stent-electrode array 109 can be connected or coupled directly to the neuromodulation unit 104 via its own transmission lead 106 or cable. In other embodiments, the stent-electrode array 109 can be coupled to the neuromodulation unit 104 via a shared transmission lead 106 or cable.

In some embodiments, the stent-electrode array 109 deployed within the venous sinus can be used to detect or record an electrophysiological signal of the subject (i.e., used as a recording electrode array). In other embodiments, the stent-electrode array 109 deployed within the venous sinus can be used to stimulate an intracorporeal target (e.g., a motor cortex) of the subject. In this manner, the stent-electrode array 109 deployed within the venous sinus can be used as a stimulating electrode array. In further embodiments, the stent-electrode array 109 deployed within the venous sinus can be used as both a recording electrode array and a stimulating electrode array (see, e.g., the stent-electrode array of FIG. 2D).

FIG. 3A also illustrates that an electrode array 102 coupled to a coiled wire 200 serving as the endovascular carrier 108 can be implanted within a superficial cerebral vein (e.g., a vein of Trolard) of the subject. The coiled wire 200 can be connected or coupled directly to the neuromodulation unit 104 via its own transmission lead 106 or cable. In other embodiments, the coiled wire 200 can be coupled to the neuromodulation unit 104 via a shared transmission lead 106 or cable.

In some embodiments, the coiled wire 200 deployed within the superficial cerebral vein can be used to detect or record an electrophysiological signal of the subject (i.e., used as a recording electrode array). In other embodiments, the coiled wire 200 deployed within the superficial cerebral vein can be used to stimulate an intracorporeal target (e.g., a motor cortex) of the subject. In this manner, the coiled wire 200 deployed within the superficial cerebral vein can be used as a stimulating electrode array. In further embodiments, the coiled wire 200 deployed within the superficial cerebral vein can be used as both a recording electrode array and a stimulating electrode array.

FIG. 3A further illustrates that an electrode array 102 coupled to an anchored wire 208 serving as the endovascular carrier 108 can be implanted within a deep cerebral vein (e.g., a superior thalamostriate vein) of the subject. The anchored wire 208 can be connected or coupled directly to the neuromodulation unit 104 via its own transmission lead 106 or cable. In other embodiments, the anchored wire 208 can be coupled to the neuromodulation unit 104 via a shared transmission lead 106 or cable.

In some embodiments, the anchored wire 208 deployed within the deep cerebral vein can be used to detect or record an electrophysiological signal of the subject (i.e., used as a recording electrode array). In other embodiments, the anchored wire 208 deployed within the deep cerebral vein can be used to stimulate an intracorporeal target (e.g., an anterior nucleus of thalamus) of the subject. In this manner, the anchored wire 208 deployed within the deep cerebral vein can be used as a stimulating electrode array. In further embodiments, the anchored wire 208 deployed within the deep cerebral vein can be used as both a recording electrode array and a stimulating electrode array.

FIG. 3A also illustrates that an electrode array 102 coupled to a stent-electrode array 109 serving as the endovascular carrier 108 can be implanted within an internal jugular vein superior to (or above) the jugular foramen of the subject. In some embodiments, the entire stent-electrode array 109 can be implanted in the internal jugular vein superior to the jugular foramen.

In other embodiments, at least part of the stent-electrode array 109 can be implanted in the internal jugular vein superior to the jugular foramen. Implantation of the stent-electrode array 109 superior to the jugular foramen will be discussed in more detail in later sections.

In some embodiments, the stent-electrode array 109 implanted within the internal jugular foramen can be used to stimulate an intracorporeal target (e.g., a superior ganglion of the vagus nerve) of the subject. In this manner, the stent-electrode array 109 implanted within the internal jugular vein can be used as a stimulating electrode array.

FIG. 3A further illustrates that an electrode array 102 coupled to an endovascular carrier 108 (e.g., a coiled wire 200, a stent-electrode array 109, or an anchored wire 208,) can be used as a recording electrode array to record an electrophysiological signal indicating a heart rate or change in heart rate (e.g., ictal tachycardia) of the subject. This cardiac signal can be associated or correlated with the onset of epileptic seizures. For example, this electrophysiological signal can be a cardiac arrhythmia known to be associated or correlated with a high likelihood of epileptic seizure onset.

As shown in FIG. 3A, the neuromodulation unit 104 can be implanted inferior to the head and neck of the subject. For example, as shown in FIG. 3A, the neuromodulation unit 104 can be implanted within a pectoral region of the subject (e.g., beneath the pectoralis major muscle).

As previously discussed, in some embodiments, the pulse generator 110 can be part of the neuromodulation unit 104. In other embodiments, the pulse generator 110 can be a standalone device separate from the neuromodulation unit 104. In these embodiments, the pulse generator 110 can be implanted within a pectoral region of the subject (e.g., beneath the pectoralis major muscle).

Figure 3B:
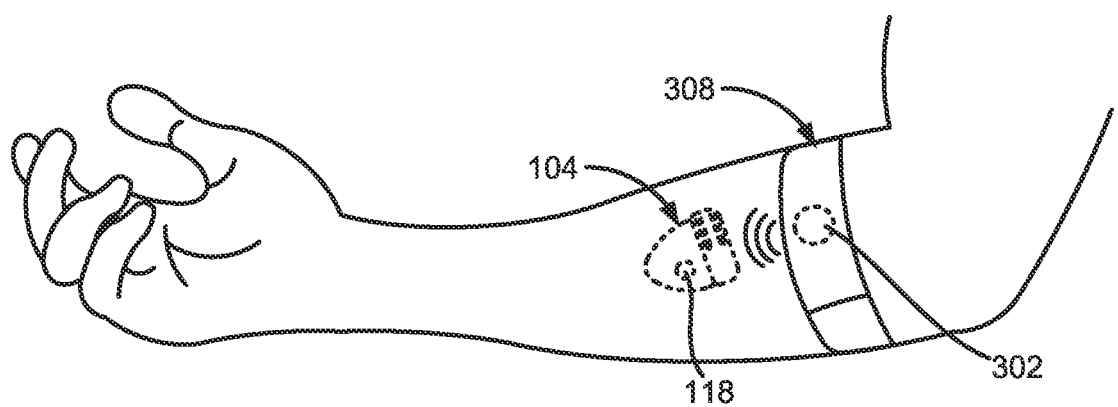
FIG. 3B illustrates a neuromodulation unit implanted within an arm of a subject.

FIG. 3B illustrates that the neuromodulation unit 104 can be implanted within a forearm of the subject. In this embodiment, the neuromodulation system 100 can comprise an extracorporeal device 300 in the form of a wearable device such as an armband 308. The implanted neuromodulation unit 104 can comprise a first magnetic component 118 (e.g., a receiving or secondary coil) and the armband 308 can comprise a second magnetic component 302 (e.g., a primary or transmission coil). The armband 308 can charge or power the neuromodulation unit 104 via electromagnetic induction.

As previously discussed, in some embodiments, the pulse generator 110 can be a standalone device separate from the neuromodulation unit 104. In these embodiments, the pulse generator 110 can be implanted within the forearm of the subject. The pulse generator 110 can comprise a first magnetic component 118 (e.g., a receiving or secondary coil) and an armband 308, serving as the extracorporeal device 300, can comprise a second magnetic component 302 (e.g., a primary or transmission coil). The armband 308 can charge or power the pulse generator 110 via electromagnetic induction.

FIG. 3A also illustrates that the extracorporeal device 300 can also be implemented as a portable handheld device 304, a wand 306, or a wearable device (e.g., bracelet or watch). The extracorporeal device 300 can be used to recharge one or more batteries within the neuromodulation unit 104, the pulse generator 110, or a combination thereof. In some embodiments, the extracorporeal device 300 can be used to activate the pulse generator 110 to transmit an electrical impulse to the stimulating electrode array.

Figure 4A:
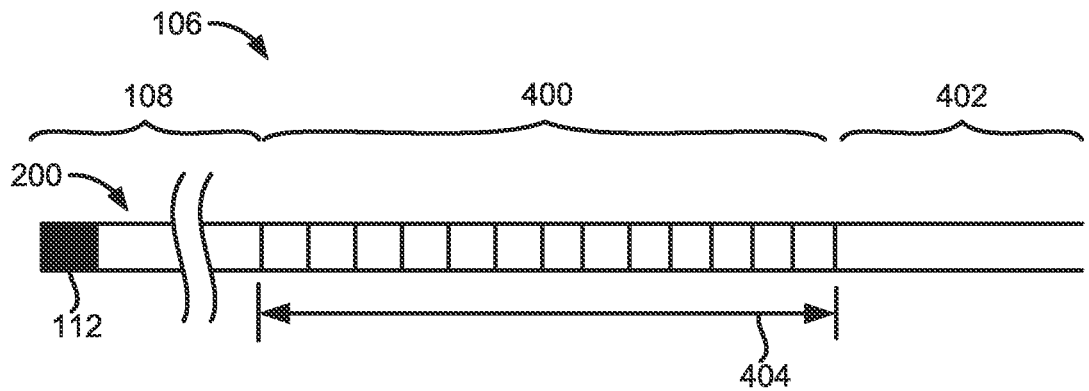
FIG. 4A-4C illustrate one embodiment of a transmission lead used to connect an electrode array to another electrode array or to the neuromodulation unit.
Figure 4B:
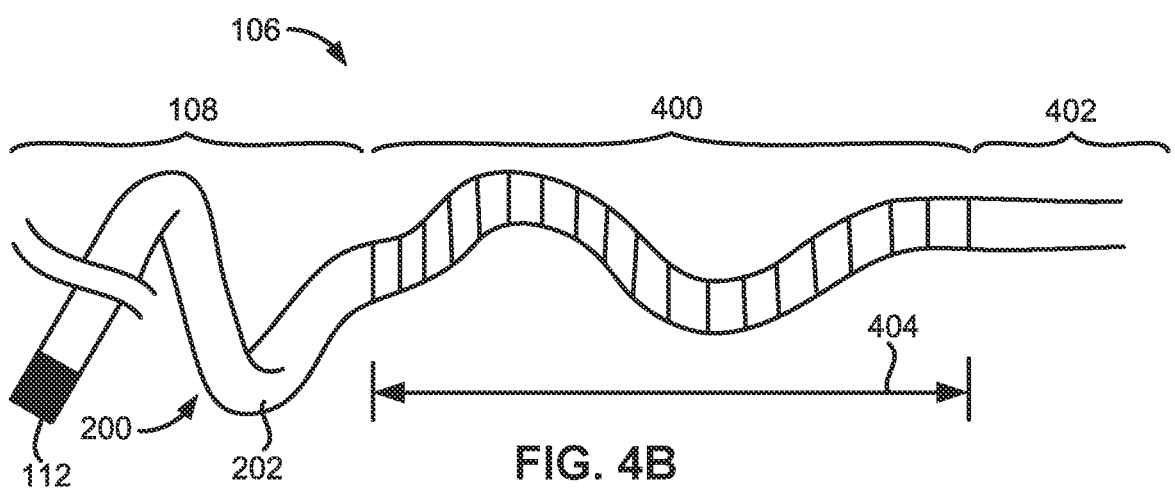
Figure 4C:
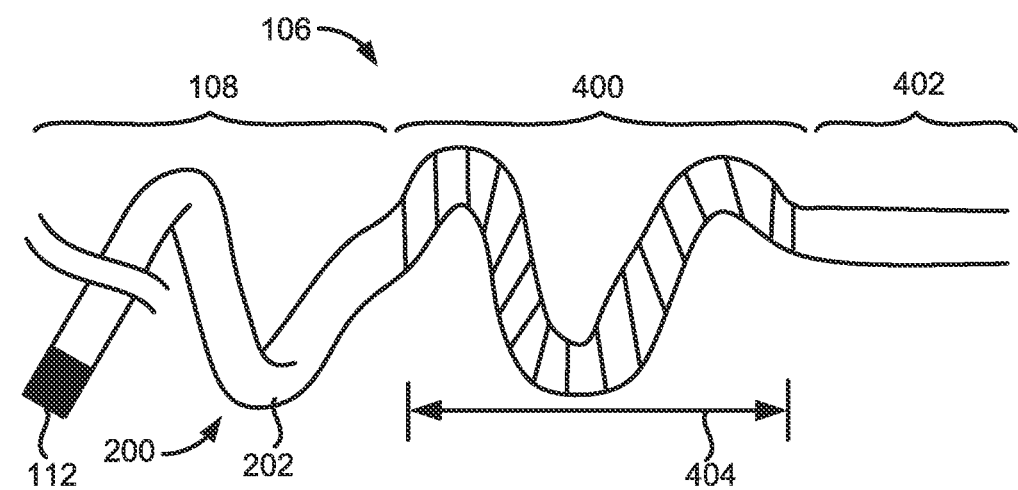

FIGS. 4A-4C illustrate one embodiment of a transmission lead 106 used to connect the electrode array 102 to the neuromodulation unit 104, the pulse generator 110, or a combination thereof. For example, the transmission lead 106 can be used to connect the first electrode array 102A or the second electrode array 102B to the neuromodulation unit 104, the pulse generator 110, or a combination thereof.

As shown in FIGS. 4A-4C, the transmission lead 106 can comprise at least one variable length segment 400 in between the endovascular carrier 108 and a transmission segment 402. A segment length 404 of the variable length segment 400 can be adjusted (e.g., shortened or lengthened) after the transmission lead 106 is deployed within a bodily vessel (e.g., vein, artery, or sinus) of the subject.

The transmission segment 402 can be a proximal segment of the transmission lead 106 configured to connect or plug in to the neuromodulation unit 104 (e.g., into the header portion 114 of the neuromodulation unit 104). The transmission segment 402 can be made of one or more conductive wires without shape memory. For example, the transmission segment 402 can be made in part of platinum wire or platinum-iridium wire. The transmission segment 402, along with other segments of the transmission lead 106, can be covered by an insulator (e.g., polyurethane) or insulating coating.

FIGS. 4A-4C illustrate that the variable length segment 400 can be connected or coupled to a proximal end of the endovascular carrier 108. For example, the endovascular carrier 108 can be a coiled wire 200 and the variable length segment 400 can be connected or coupled directly to the proximal end of the coiled wire 200.

The variable length segment 400 of the transmission lead 106 can be made in part of a shape-memory alloy. The variable length segment 400 of the transmission lead 106 can also be made of a composite material comprising a shape-memory alloy. For example, the variable length segment 400 of the transmission lead 106 can be made in part of Nitinol (e.g., Nitinol wire). In some embodiments, the variable length segment 400 of the transmission lead 106 can be made of composite clad wire or a Nitinol wire having a conductive (e.g., gold or platinum) wire core.

FIG. 4A illustrates the shape of the coiled wire 200 and the transmission lead 106 when constricted within a delivery catheter or sheath. FIG. 4B illustrates the shape of the coiled wire 200 and the transmission lead 106 when the coiled wire 200 and the transmission lead 106 are deployed out of the delivery catheter or when the delivery catheter or sheath is retracted.

As shown FIG. 4B, the variable length segment 400 of the transmission lead 106 can be configured to automatically recover a preset or pretrained shape. In some embodiments, the preset or pretrained shape can be a coiled configuration having loosely-wound coils or coils with a larger pitch or less turns than the coils of the coiled wire 200. The variable length segment 400 can automatically attain its loosely coiled configuration via shape memory when a delivery catheter or sheath carrying the variable length segment 400 is retracted.

In certain embodiments, the preset or pretrained shape of the coils formed by the variable length segment 400 can have a coil diameter less or smaller than the diameter of the anticipated deployment or implantation vessel. This ensures that the radial forces exerted by the coils on the vessel lumen walls do not prevent the coils of the variable length segment 400 from shifting, contracting, or expanding within the bodily vessel of the subject. In some instances, this contraction and expansion can allow the segment length 404 of the variable length segment 400 to vary (e.g., shorten or lengthen). For example, the variable length segment 400 can lengthen by pulling on a proximal (or distal) end of the variable length segment 400. The variable length segment 400 can be shortened by pushing on a proximal end of the variable length segment 400 when an endovascular carrier 108 coupled to a distal end of the variable length segment 400 is implanted or otherwise secured within a deployment vessel. The variable length segment 400 can also be shortened by pushing on a distal end of the variable length segment 400 when an endovascular carrier 108 coupled to a proximal end of the variable length segment 400 is implanted or otherwise secured within a deployment vessel.

In some embodiments, the variable length segment 400 can attain a coiled configuration when or only when a pushing force is applied to the variable length segment 400 to compel or urge the variable length segment 400 into the coiled configuration.

In further embodiments, the variable length segment 400 can have little or no shape memory and the variable length segment 400 can be a segment of the transmission lead 106 configured to curl up or deform when a pushing force is applied to the variable length segment 400.

One technical problem faced by the applicants is how to design an implantable neuromodulation system comprising endovascular carriers connected or coupled by transmission leads when the distance between such endovascular carriers or the distance between such endovascular carriers and an implantable neuromodulation unit or pulse generator differs by patient or treatment regimen. For example, differences in neck and torso lengths among subjects and where such endovascular carriers are implanted within each subject requires a neuromodulation system that can adapt to different sized anatomy and different implantation requirements. One advantage of the neuromodulation system 100 disclosed herein is the unique transmission leads 106 comprising the variable length segment 400 disclosed herein that can allow the neuromodulation system 100 to be adapted to different sized patients and patients with different implantation requirements.

In some embodiments, the transmission lead 106 can have a lead diameter of between 0.5 mm and 1.5 mm. More specifically, the transmission lead 106 can have a lead diameter of between 0.5 mm and 1.0 mm.

In some embodiments, the transmission lead 106, or segments thereof, can be covered by an insulator or insulating coating. For example, the transmission lead 106, or segments thereof, can be covered by polyurethane or a polyurethane coating.

In some embodiments, at least a segment of the transmission lead 106 can be a cable comprising multiple conductive wires or transmission wires coupled to the various electrodes 112 of the electrode array 102. For example, the transmission lead 106 can be a stranded cable comprising a plurality of conductive wires twisted and bundled together and covered by an insulator or insulating material.

Figure 5A:
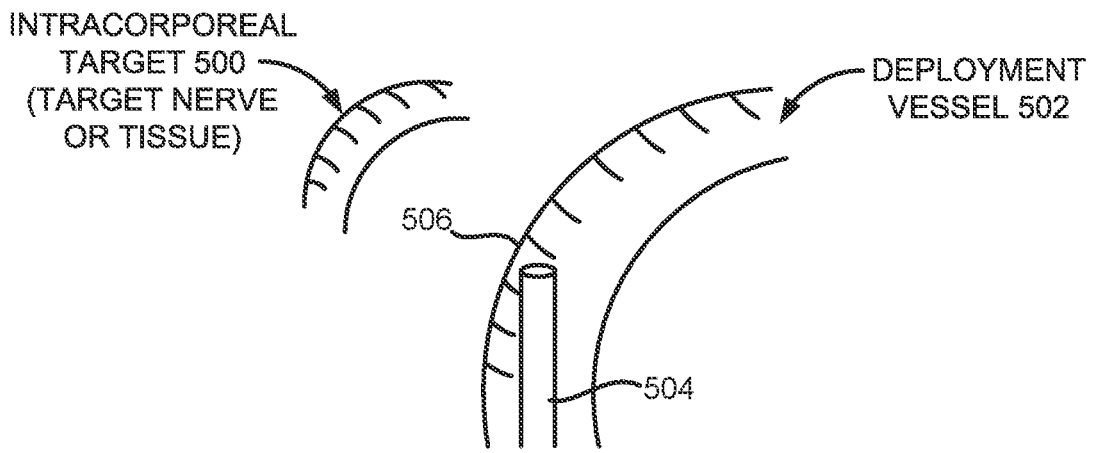
FIG. 5A-5C illustrate an example method of implanting an embodiment of an electrode array.
Figure 5B:
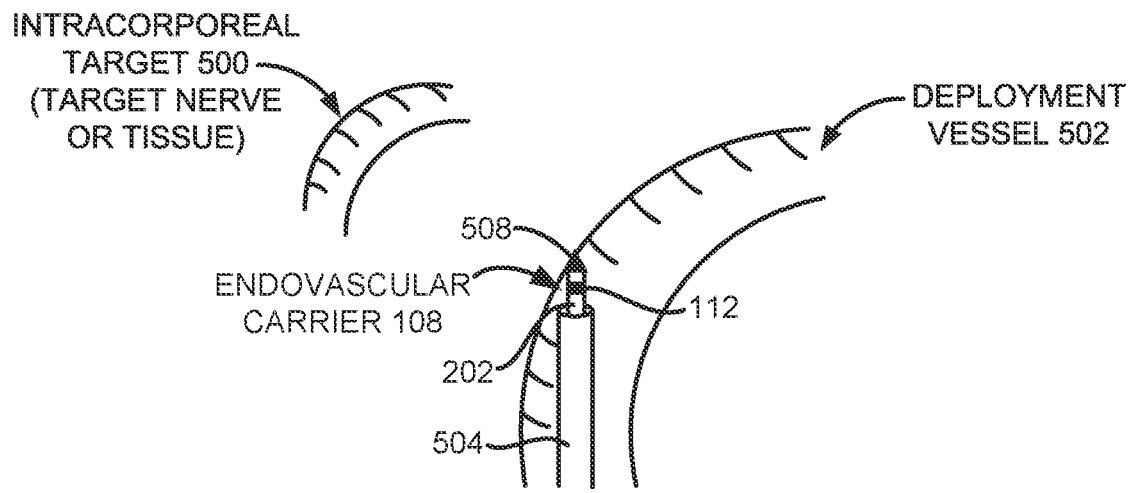
Figure 5C:
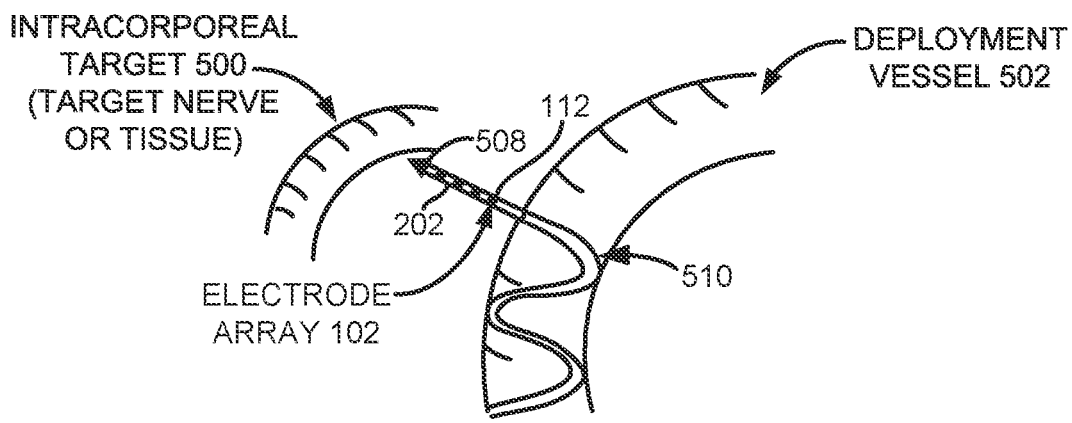

FIGS. 5A-5C illustrate an example method of implanting an embodiment of an electrode array 102 (e.g., any of the first electrode array 102A or the second electrode array 102B). The method can be used when an intracorporeal target 500 is close to but not adjacent to a vessel 502 used to deliver or deploy the electrode array 102.

As shown in FIGS. 5A and 5B, when a delivery catheter 504 is moved into position near a vessel wall 506, an endovascular carrier 108 carrying the electrode array 102 can be deployed out of the delivery catheter 504. In the embodiment shown in FIGS. 5A-5C, the endovascular carrier 108 can be an anchored wire 208 having the electrode array 102 coupled along a segment of a biocompatible wire 202 or microwire (see, also, FIG. 2C).

The wire 202 or microwire can comprise a sharp distal end in the form of a penetrating barb 508 or penetrating anchor coupled or detachably coupled to the distal end of the wire 202 or microwire. The penetrating barb 508 or penetrating anchor can allow the wire 202 or microwire to penetrate or create a puncture in the vessel wall 506 to allow the wire 202 or microwire to extend through the vessel wall 506. The wire 202 or microwire can then direct the electrode array 102 closer to the intracorporeal target 500 (e.g., the target nerve or brain region) such that the electrode array 102 is positioned at or in close proximity to the intracorporeal target 500.

FIG. 5C illustrates that once the delivery catheter 504 is retracted, a wire segment 510 proximal to the electrode array 102 can automatically take the shape of a coil. The coil shape of the wire segment 510 can be pre-set prior to being introduced into the delivery catheter 504. For example, the wire segment 510 can have a lead diameter of about 1.0 mm (or less than 1.0 mm) and the vessel 502 can have a vessel diameter of about 6.0 mm. Once the delivery catheter 504 is removed, the wire segment 510 can take the shape of a coil having a coil diameter of greater than 6.0 mm. The wire segment 510 can self-expand until the coil pushes against the internal vessel walls to secure the wire segment 510 to the internal vessel walls. In this embodiment, the wire segment 510 proximal to the electrode array 102 can be used to also secure the endovascular carrier 108. With the wire segment 510 and the electrode array 102 in place, the penetrating barb 508 can be removed by a stylet or other device extending through the delivery catheter 504.

Figure 6:
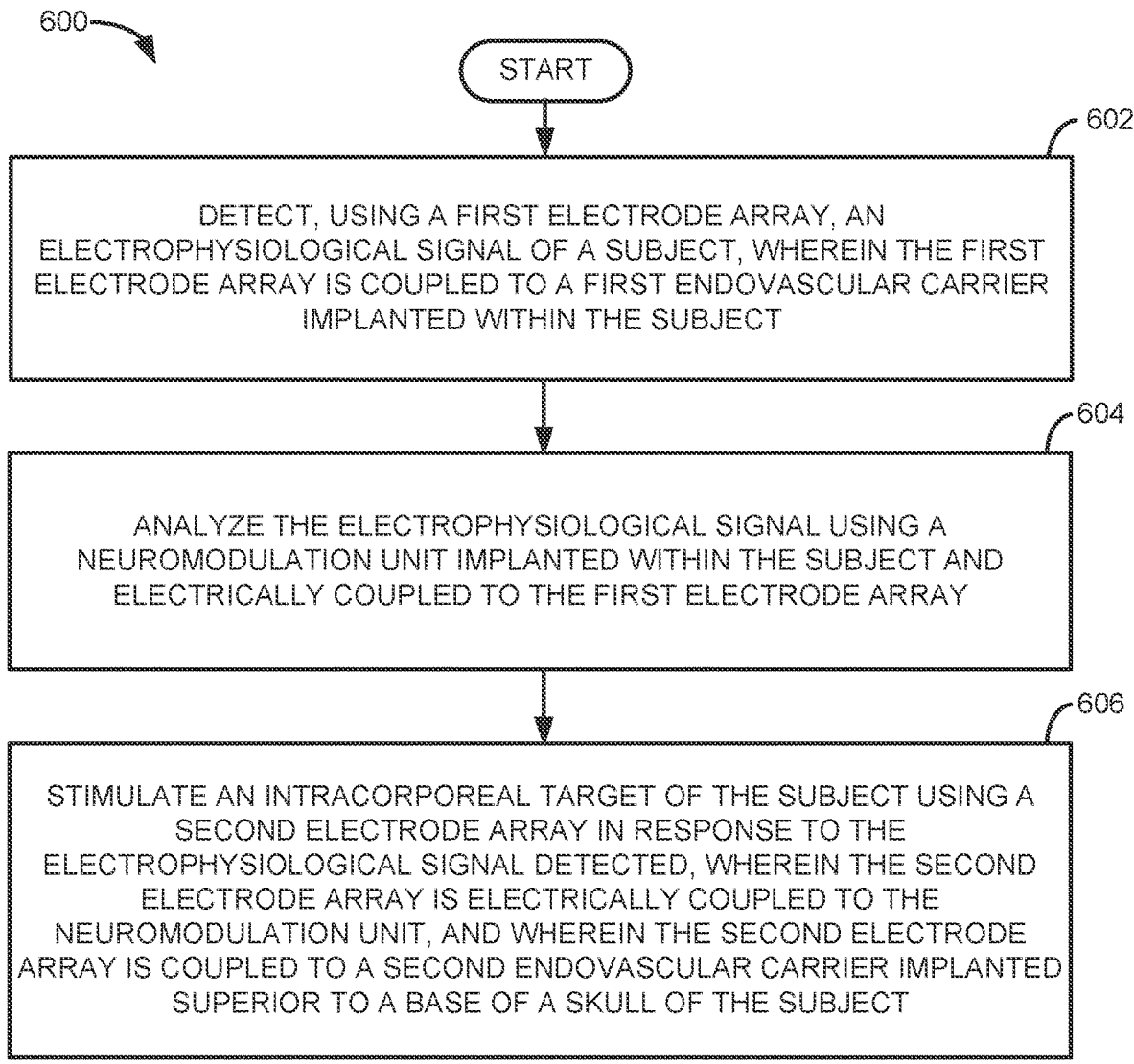
FIG. 6 illustrates one embodiment of a method of treating epilepsy.

FIG. 6 illustrates one embodiment of a method 600 of treating epilepsy. The method 600 can comprise detecting, using a first electrode array 102A, an electrophysiological signal of a subject in step 602. In this manner, the first electrode array 102A can act as a recording electrode array. The first electrode array 102A can be affixed, secured, otherwise coupled to the first endovascular carrier 108A (e.g., spaced out along a length of the first endovascular carrier 108A and/or coupled to a radially outer portion of the first endovascular carrier 108A). The first endovascular carrier 108A can be implanted within an artery, vein, or sinus of the subject. Possible implantation sites for the first endovascular carrier 108A will be discussed in more detail in the following sections.

The method 600 can also comprise analyzing the electrophysiological signal using a neuromodulation unit 104 implanted within the subject and electrically coupled to the first electrode array 102A via one or more conductive leads and/or a transmission lead 106 in step 604. The neuromodulation unit 104 can be configured to analyze the electrophysiological signal by (i) comparing the signal detected against one or more thresholds (e.g., detecting a spike in the signal), (ii) detecting certain signal patterns or rhythmic activity in specific frequency ranges, (iii) comparing absolute sample-to-sample amplitude differences within a predetermined time window, (iv) measuring a change in signal energy, or a combination thereof.

The method 600 can also comprise stimulating an intracorporeal target of the subject using a second electrode array 102B in response to the electrophysiological signal detected in step 606. In this manner, the second electrode array 102B can act as a stimulating electrode array. The second electrode array 102B can be affixed, secured, or otherwise coupled to the second endovascular carrier 108B (e.g., spaced out along a length of the second endovascular carrier 108B and/or coupled to a radially outer portion of the second endovascular carrier 108B). The second endovascular carrier 108B can be implanted within an artery, vein, or sinus of the subject superior to a base of the skull of the subject.

Figure 7:
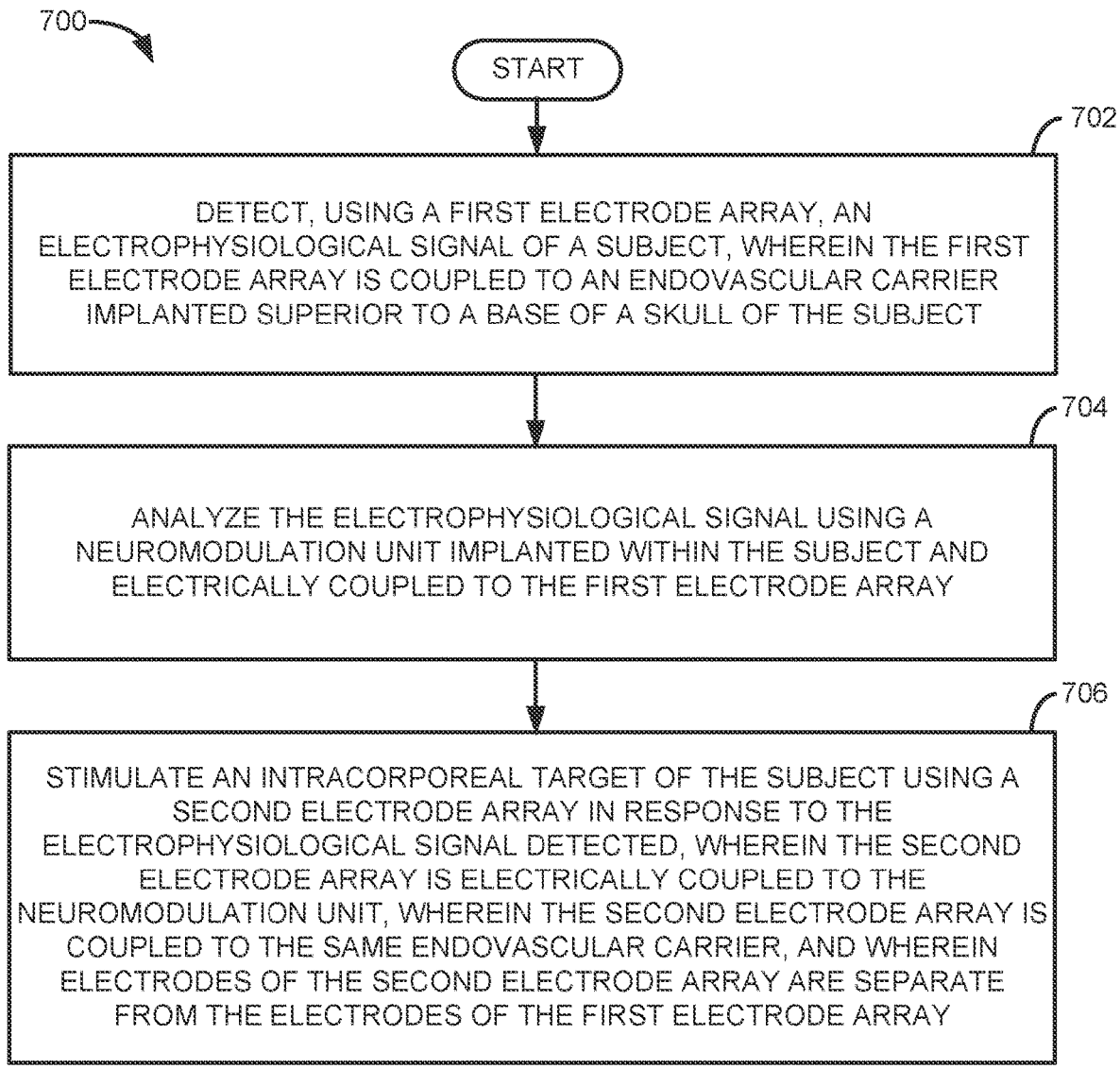
FIG. 7 illustrates another embodiment of a method of treating epilepsy.

FIG. 7 illustrates another embodiment of a method 700 of treating epilepsy. The method 700 can comprise detecting, using a first electrode array 102A, an electrophysiological signal of a subject in step 702. In this manner, the first electrode array 102A can act as a recording electrode array. The first electrode array 102A can be affixed, secured, otherwise coupled to an endovascular carrier 108 implanted endovascularly within an artery, vein, or sinus of the subject superior to a base of the skull of the subject. For example, the endovascular carrier 108 can be the endovascular carrier 214 depicted in FIG. 2D.

The first electrode array 102A can be spaced out along a length of the endovascular carrier 108 and/or coupled to a radially outer portion of the endovascular carrier 108. Possible implantation sites for the endovascular carrier 108 will be discussed in more detail in the following sections.

The method 700 can also comprise analyzing the electrophysiological signal using a neuromodulation unit 104 implanted within the subject and electrically coupled to the first electrode array 102A via one or more conductive leads and/or a transmission lead 106 in step 704. The neuromodulation unit 104 can be configured to analyze the electrophysiological signal by (i) comparing the signal detected against one or more thresholds (e.g., detecting a spike in the signal), (ii) detecting certain signal patterns or rhythmic activity in specific frequency ranges, (iii) comparing absolute sample-to-sample amplitude differences within a predetermined time window, (iv) measuring a change in signal energy, or a combination thereof.

The method 700 can also comprise stimulating an intracorporeal target of the subject using a second electrode array 102B in response to the electrophysiological signal detected in step 706. The second electrode array 102B can be spaced out along a length of the endovascular carrier 108 and/or coupled to a radially outer portion of the endovascular carrier 108. In this manner, the second electrode array 102B can act as a stimulating electrode array. The second electrode array 102B can be affixed, secured, or otherwise coupled to the same endovascular carrier 108 (e.g., spaced out along a length of the endovascular carrier 108 and/or coupled to a radially outer portion of the endovascular carrier 108). The electrodes of the second electrode array 102B can be separate from the electrodes of the first electrode array 102A.

Although FIGS. 6 and 7 disclose methods of treating epilepsy, it is contemplated by this disclosure that the neuromodulation system 100 disclosed herein can also be used in treating other disorders or conditions including headaches, bipolar disorder, obesity, Alzheimer's disease, Parkinson's disease, rheumatoid arthritis, or inflammatory bowel disease. For example, a method of treating one of the aforementioned conditions/disorders can comprise detecting, using a first electrode array 102A, an electrophysiological signal of a subject associated with or related to an onset of symptoms related to the condition/disorder. The first electrode array 102A can be coupled to a first endovascular carrier 108A implanted superior to a base of the skull of the subject. The method can also comprise analyzing the electrophysiological signal using a neuromodulation unit 104 implanted within the subject and electrically coupled to the first electrode array 102A. The method can further comprise stimulating an intracorporeal target of the subject using a second electrode array 102B in response to the electrophysiological signal detected. The second electrode array 102B can be coupled to a second endovascular carrier 108B implanted endovascularly within the subject and electrically coupled to the neuromodulation unit 104. For example, stimulating the intracorporeal target can comprise generating an electrical impulse using a pulse generator 110 of the neuromodulation unit 104. Stimulating the intracorporeal target can alleviate or lessen a symptom or contributing factor of the condition/disorder.

Figure 8A:
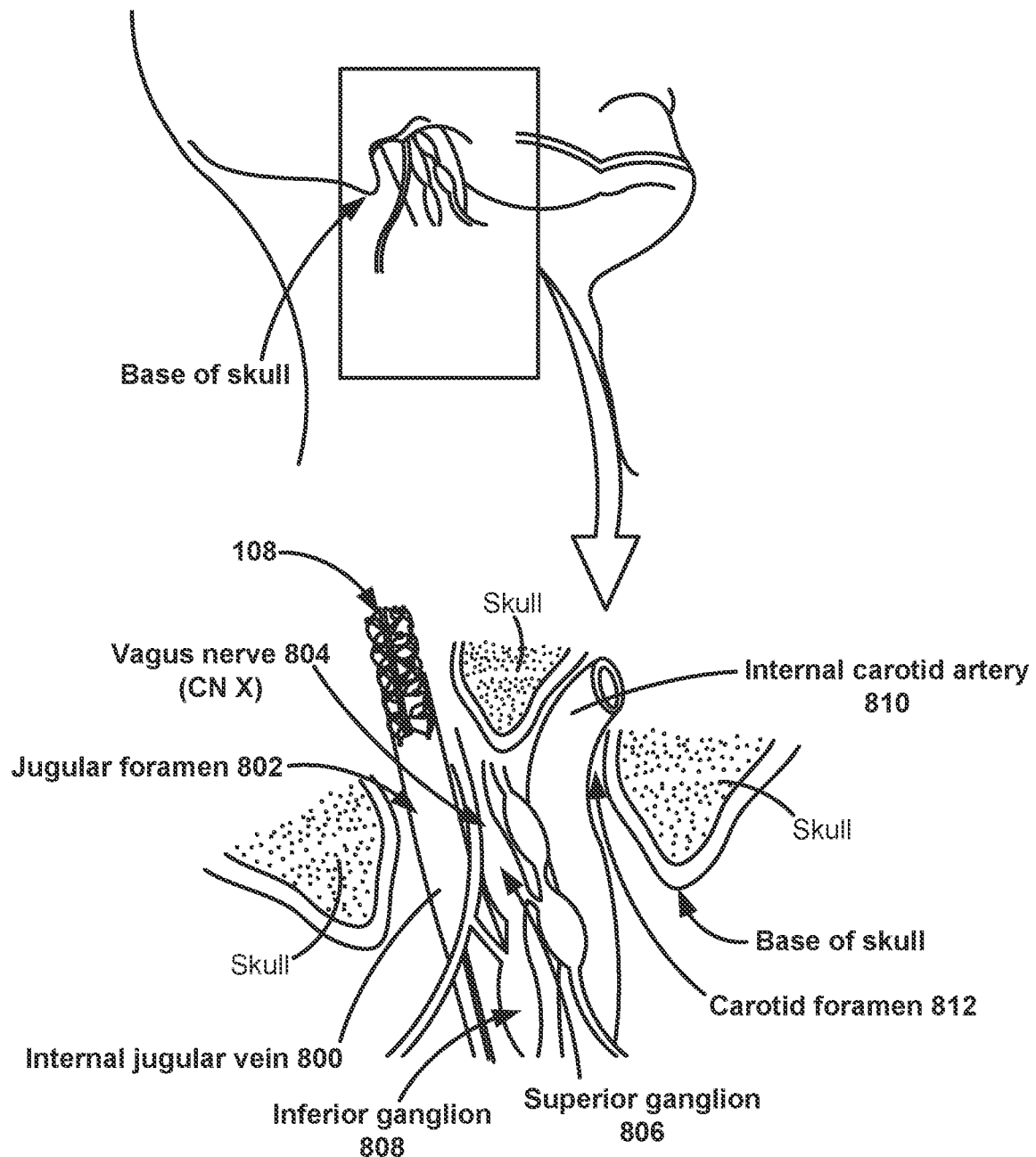
FIG. 8A illustrates an embodiment of an endovascular carrier implanted within an internal jugular vein of a subject.

FIG. 8A illustrates that the endovascular carrier 108 (including any of the first endovascular carrier 108A or the second endovascular carrier 108B) can be implanted within the internal jugular vein 800 (e.g., the right internal jugular vein or the left internal jugular vein) superior to a jugular foramen 802 of the subject. The jugular foramen 802 is a cavity formed in the inferior portion of the base of the subject's skull. The jugular foramen 802 is formed by the petrous part of the temporal bone anteriorly and the occipital bone posteriorly.

When the endovascular carrier 108 is implanted within the internal jugular vein 800 superior to the jugular foramen 802, the electrode array 102 coupled to the endovascular carrier 108 can be used to stimulate a vagus nerve 804 of the subject. In certain embodiments, the intracorporeal target or stimulation target can be the superior ganglion 806 of the vagus nerve 804. In other embodiments, the intracorporeal target or the stimulation target can be both the superior ganglion 806 and the inferior ganglion 808 of the vagus nerve 804.

In some embodiments, a method of treating epilepsy can comprise implanting a first electrode array 102A coupled to a first endovascular carrier 108A in a cerebral or cortical vein or sinus of the subject to record an electrophysiological signal of the subject associated or correlated with or indicative of the onset of an epileptic seizure. The method can also comprise implanting a second electrode array 102B coupled to a second endovascular carrier 108B (e.g., the stent-electrode array 109) in the internal jugular vein 800 superior to the jugular foramen 802 to stimulate the vagus nerve 804 of the subject. A neuromodulation unit 104 electrically coupled to the first electrode array 102A and the second electrode array 102B can analyze the electrophysiological signal and instruct a pulse generator 110 of the neuromodulation unit 104 to generate an electrical impulse to stimulate the vagus nerve 804.

The electrical impulse can be biphasic, monophasic, sinusoidal, or a combination thereof. For example, the electrical impulse can be charge-balanced biphasic pulses. The pulse generator 110 can generate the electrical impulse by increasing a current amplitude of the electrical impulse from 0.25 mA to up to 2 mA in 0.1 mA steps and increasing a voltage of the electrical impulse from 0 V to up to 10 V in 0.25 V steps. The electrical impulse generated can have a pulse width of between 250 µS to about 500 µS. A timing parameter of the electrical impulse can also be adjusted to allow for different stimulation timing patterns. The electrical impulse generated can have a frequency between 10 Hz and 30 Hz.

In some embodiments, at least part of the endovascular carrier 108 can be implanted within the internal jugular vein 800 superior to the jugular foramen 802. In additional embodiments, at least part of the endovascular carrier 108 can be implanted within a branch or tributary of the internal jugular vein 800.

In additional embodiments, the endovascular carrier 108 can be implanted within the internal carotid artery 810 superior to the base of the skull of the subject. In further embodiments, the endovascular carrier 108 can be implanted within the internal carotid artery 810 superior to a carotid foramen 812 of the subject. In other embodiments, at least part of the endovascular carrier 108 can be implanted within the internal carotid artery 810 superior to the base of the skull of the subject. In further embodiments, at least part of the endovascular carrier 108 can be implanted within the internal carotid artery 810 superior to the carotid foramen 812. In these and other embodiments, the intracorporeal target can be the vagus nerve 804 of the subject.

Although FIG. 8A illustrates the endovascular carrier 108 as a stent-electrode array 109, it is contemplated by this disclosure that any of the endovascular carriers 108 disclosed herein (including the coiled wire 200 or the anchored wire 208) can be implanted within the internal jugular vein 800. Moreover, any of the endovascular carriers 108 disclosed herein (including any of the stent-electrode array 109, the coiled wire 200, or the anchored wire 208) can be implanted within the internal carotid artery 810.

Figure 8B:
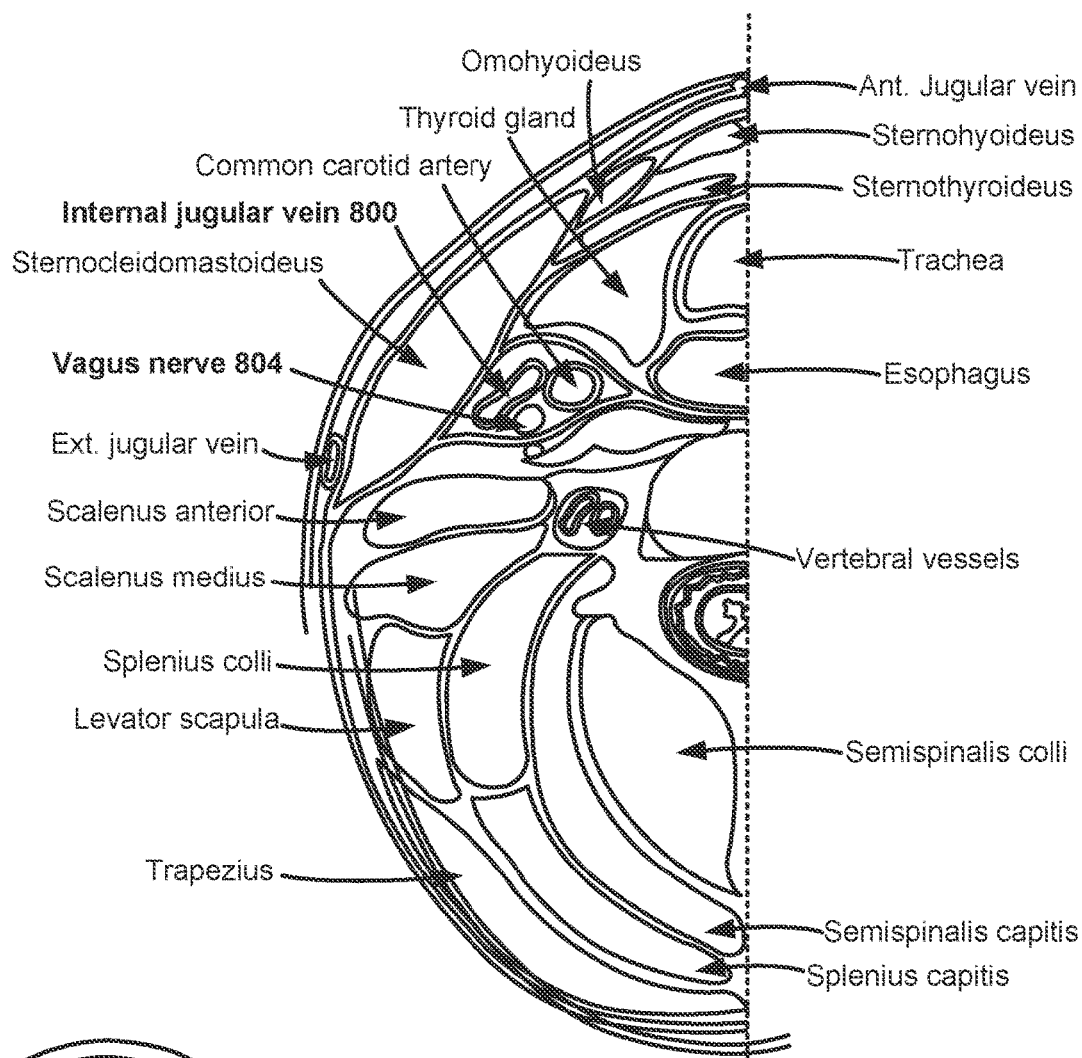
FIG. 8B illustrates a partial sectional view of a transverse section of a subject at the level of the C6 vertebra showing the vagus nerve and surrounding vessels.
Figure 8C:
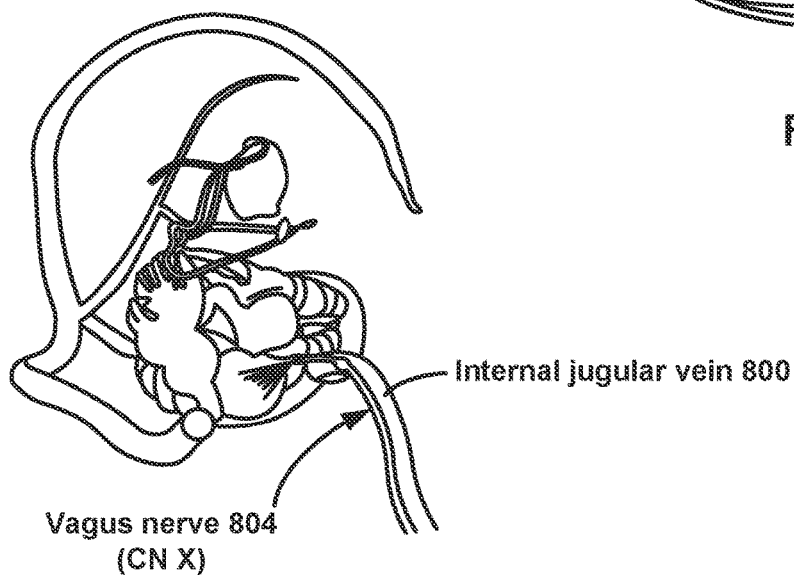
FIG. 8C illustrates a proximity of the internal jugular vein to the vagus nerve.
Figure 9A:
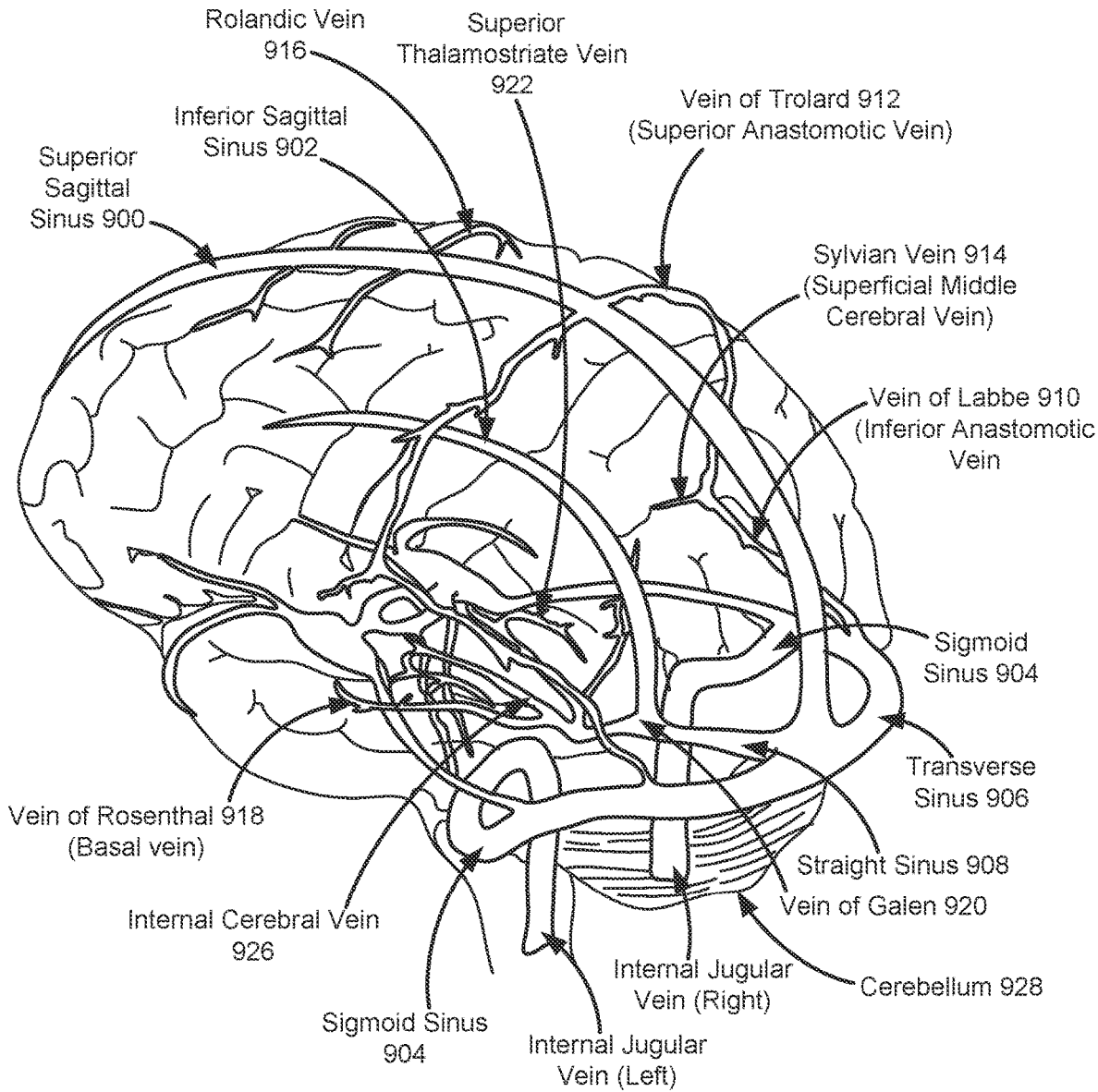
FIGS. 9A-9G illustrate certain veins and sinuses that can serve as implantation sites for the endovascular carriers.
Figure 9B:
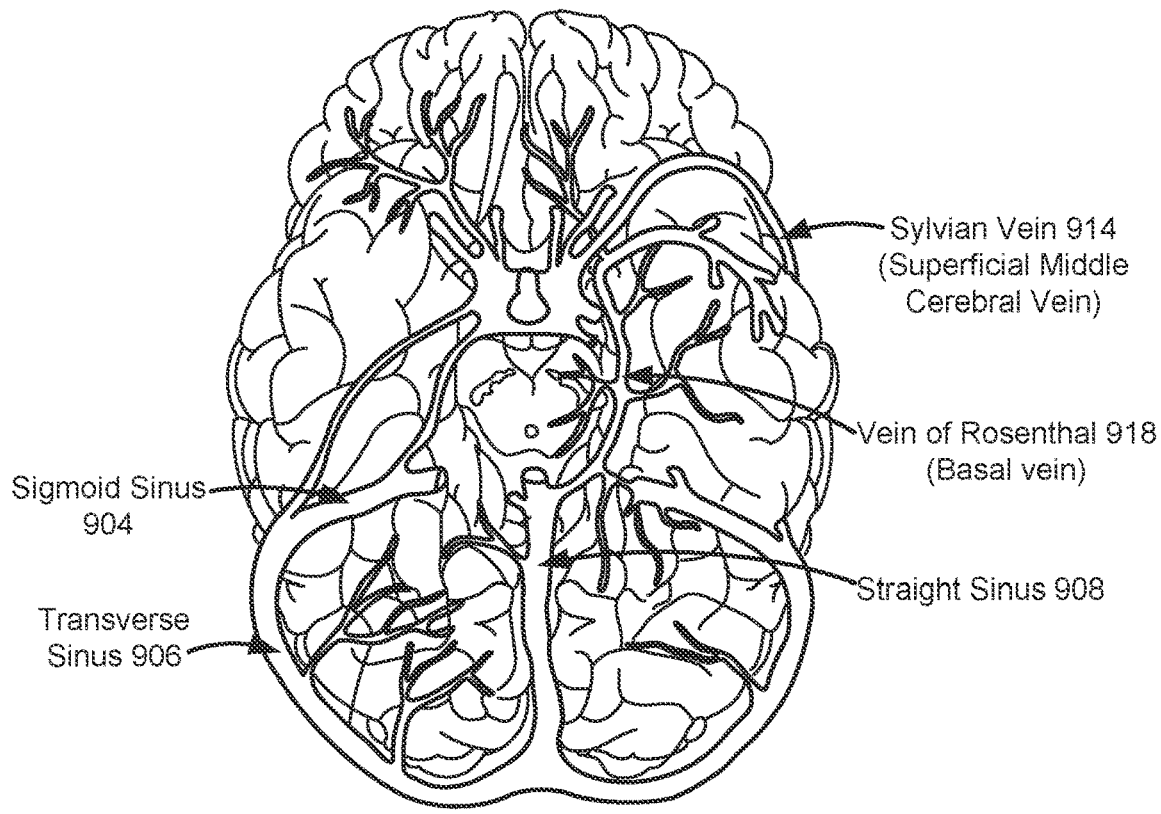
Figure 9C:
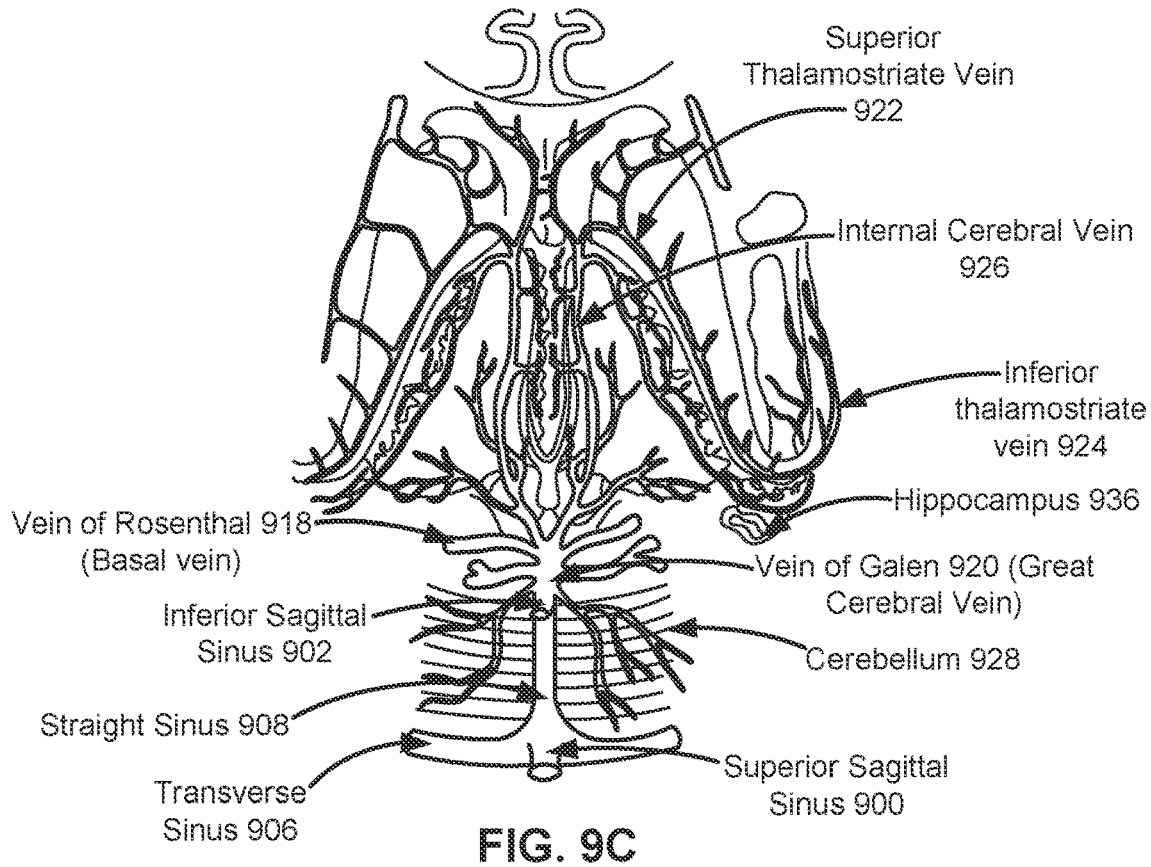
Figure 9D:
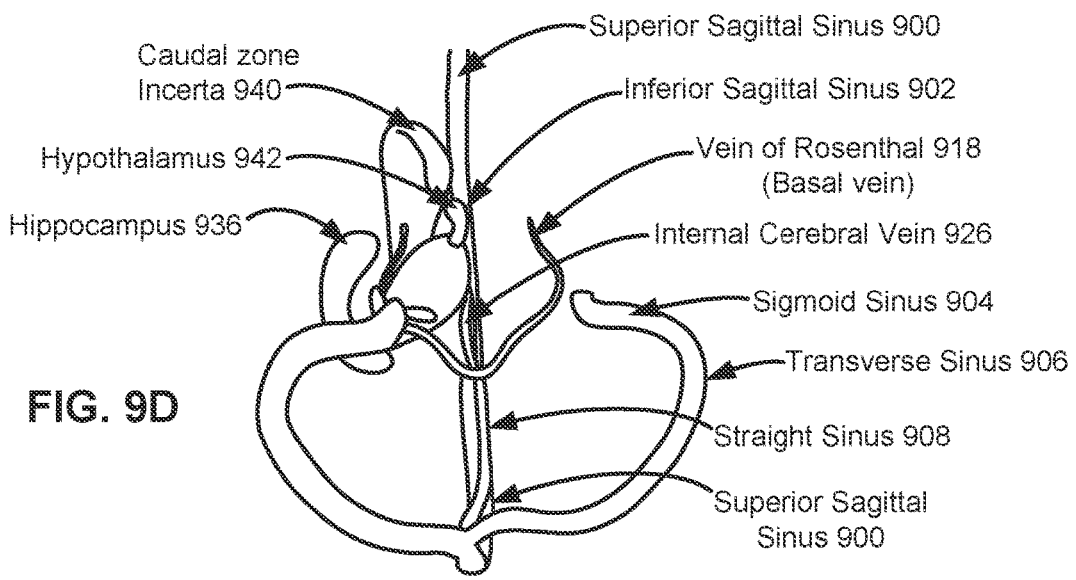
Figure 9E:
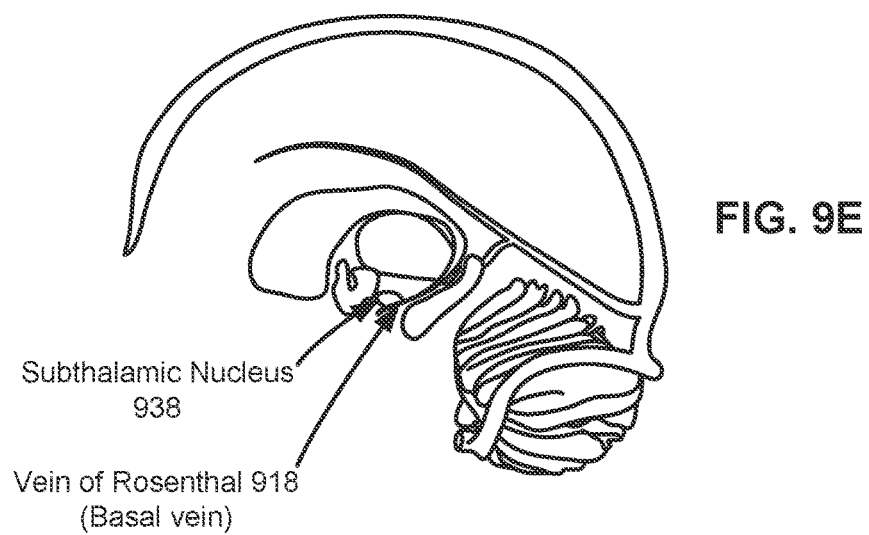
Figure 9F:
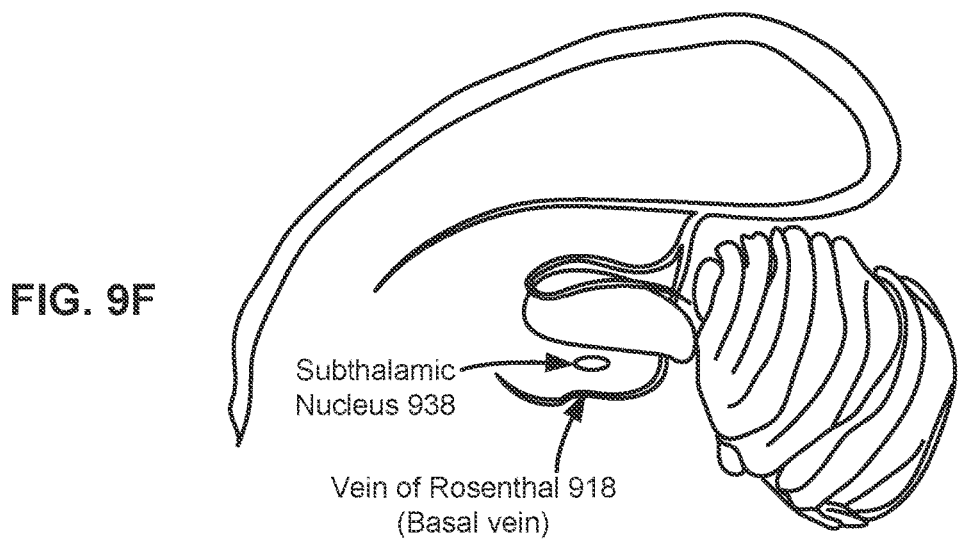
Figure 9G:
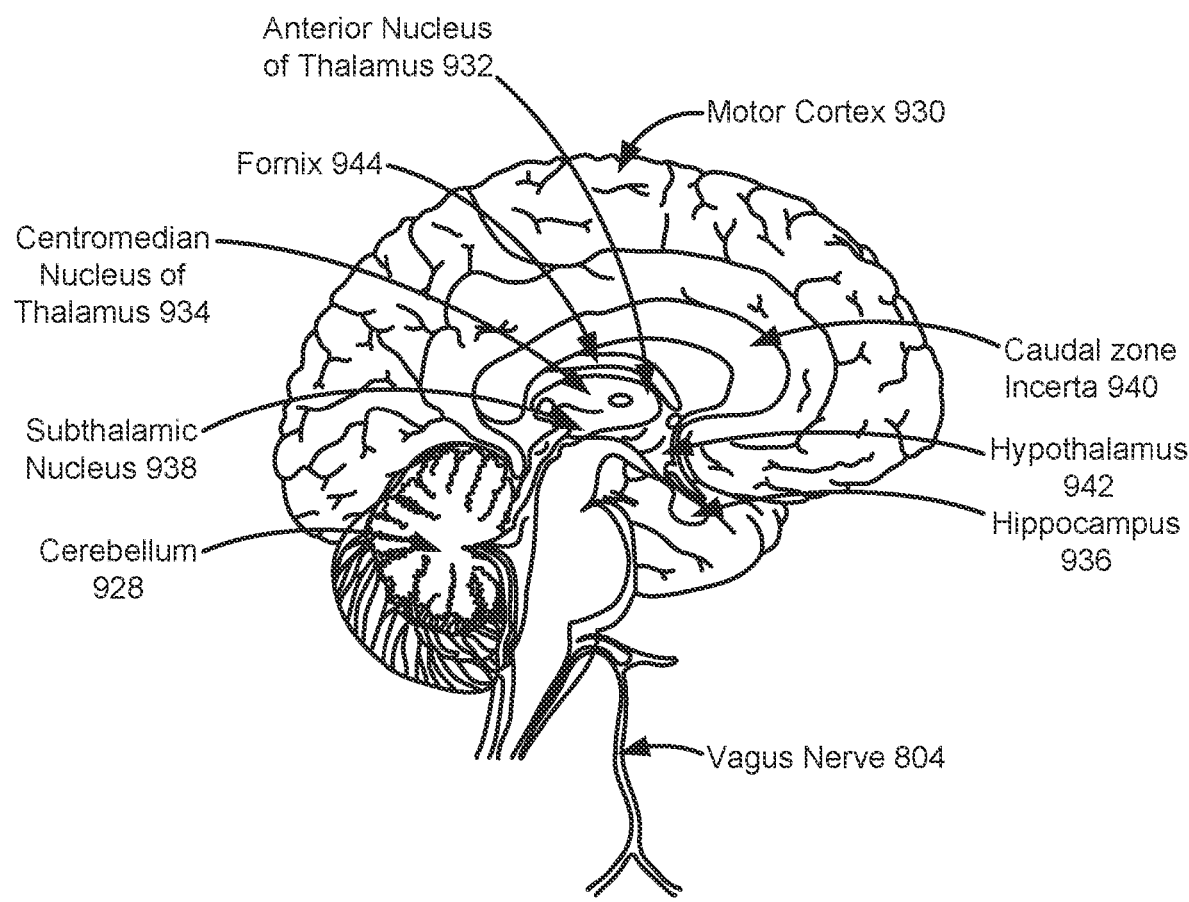

FIGS. 8B and 8C illustrate a proximity of the vagus nerve 804 to the internal jugular vein 800. In most subjects, at least part of the vagus nerve 804 extending through the neck and into the skull of the subject is in contact with the internal jugular vein 800 or adjacent to the internal jugular vein 800 (i.e., separated from the internal jugular vein 800 by less than 2.0 mm).

For example, FIG. 8B illustrates a partial sectional view of a transverse section of a subject at the level of the C6 vertebra showing the vagus nerve 804 and surrounding vessels, including the internal jugular vein 800. As previously discussed, the internal jugular vein 800 can serve as a possible implantation site for an endovascular carrier 108 carrying an electrode array 102 (e.g., a stimulating electrode array).

In some embodiments not shown in the figures, the endovascular carrier 108 can also be implanted within a common carotid artery (outside of the skull of the subject) or an external carotid artery.

One technical problem faced by the applicants is that endovascular carriers 108 implanted in vessels within the neck of the subject can wear down over time as a result of the natural motion of the neck (e.g., bending, flexion, extension, rotation, etc.). Moreover, endovascular carriers 108 implanted in vessels within the neck can also be damaged by external forces applied to the neck of the subject. One advantage of implanting the endovascular carriers 108 within the skull of the subject (e.g., in an internal carotid artery superior to a jugular foramen) is that the skull acts as a protective casing for the endovascular carrier 108 and only one or more thin transmission leads 106 extend through the neck of the subject. This can also increase patient comfort and increase the deployed lifespan of the endovascular carrier. Moreover, electrophysiological recordings taken from electrodes within the skull are less impacted by extraneous signals such as heart beating artifacts.

FIGS. 9A-9G illustrate certain veins and sinuses of the subject that can serve as implantation sites for the endovascular carriers 108 carrying the electrode arrays 102. Moreover, FIGS. 9A-9G also illustrate certain intracorporeal targets or stimulation targets that can be stimulated as part of a treatment for epilepsy or other disorders/conditions.

In some embodiments, the first endovascular carrier 108A carrying the first electrode array 102A can be implanted within a venous sinus of the subject. For example, the first endovascular carrier 108A carrying the first electrode array 102A can be implanted within a superior sagittal sinus 900, an inferior sagittal sinus 902, a sigmoid sinus 904, a transverse sinus 906, or a straight sinus 908.

In other embodiments, the first endovascular carrier 108A carrying the first electrode array 102A can be implanted within a superficial cerebral vein of the subject. For example, the first endovascular carrier 108A carrying the first electrode array 102A can be implanted within at least one of a vein of Labbe 910, a vein of Trolard 912, a Sylvian vein 914, and a Rolandic vein 916.

The first endovascular carrier 108A carrying the first electrode array 102A can also be implanted within a deep cerebral vein of the subject. For example, the first endovascular carrier 108A carrying the first electrode array 102A can be implanted within at least one of a vein of Rosenthal 918, a vein of Galen 920, a superior thalamostriate vein 922, an inferior thalamostriate vein 924, and an internal cerebral vein 926.

In further embodiments, the first endovascular carrier 108A carrying the first electrode array 102A can also be implanted within at least one of a central sulcal vein, a post-central sulcal vein, and a pre-central sulcal vein. In additional embodiments, the first endovascular carrier 108A can also be implanted or configured to be implanted within a vessel extending through a hippocampus or amygdala of the subject.

Once implanted, the first electrode array 102A can be configured to detect or record an electrophysiological signal of the subject associated or correlated with the onset of epileptic seizures. In some embodiments, the electrophysiological signal can be a local field potential (LFP) and/or an intracranial/cortical EEG measured within a cerebral or cortical vessel (e.g., a venous sinus or cortical vein). In other embodiments, the electrophysiological signal can be an electrocorticography (ECoG) signal.

As previously discussed, the neuromodulation unit 104 can further comprise a telemetry unit 120 or telemetry module (e.g., a telemetry hardware module, a telemetry software module, or a combination thereof). The telemetry unit 120 can be configured to analyze the electrophysiological signal detected or recorded by the first electrode array 102A. For example, the one or more processors of the neuromodulation unit 104 (or the telemetry unit 120 within the neuromodulation unit 104) can be programmed to execute instructions stored in the one or more memory units to analyze the electrophysiological signal by: (i) comparing the signal detected against one or more thresholds (e.g., detecting a spike in the signal), (ii) detecting certain signal patterns or rhythmic activity in specific frequency ranges. (iii) comparing absolute sample-to-sample amplitude differences within a predetermined time window, (iv) measuring a change in signal energy, or a combination thereof. The neuromodulation unit 104 can then instruct a pulse generator 110 (e.g., a pulse generator provided as part of the neuromodulation unit 104 or a pulse generator separate from the neuromodulation unit 104) to generate an electrical impulse to stimulate an intracorporeal target or stimulation target via the second electrode array 102B coupled to a second endovascular carrier 108B.

As previously discussed, when the intracorporeal target is a vagus nerve of the subject, the second endovascular carrier 108B can be implanted within an internal jugular vein (either a right internal jugular vein or a left internal jugular vein) or an internal carotid artery.

In other embodiments, the intracorporeal target or stimulation target can be the cerebellum 928 of the subject. In these embodiments, the second endovascular carrier 108B carrying the second electrode array 102B can be implanted within at least one of a sigmoid sinus 904 and a straight sinus 908 of the subject. Moreover, the second endovascular carrier 108B carrying the second electrode array 102B can also be implanted within a transverse sinus 906 of the subject. At least part of the cerebellum 928 is adjacent to the sigmoid sinus 904, the straight sinus 908, and the transverse sinus 906 (i.e., separated by less than 2.0 mm).

In additional embodiments, the intracorporeal target or stimulation target can be the motor cortex 930 of the subject. In these embodiments, the second endovascular carrier 108B carrying the second electrode array 102B can be implanted within at least one of an inferior sagittal sinus 902, a central sulcal vein, a post-central sulcal vein, and a pre-central sulcal vein of the subject. Moreover, the second endovascular carrier 108B carrying the second electrode array 102B can also be implanted within a superior sagittal sinus 900 of the subject. At least part of the motor cortex 930 is adjacent to the superior sagittal sinus 900, the central sulcal vein, the post-central sulcal vein, and the pre-central sulcal vein (i.e., separated by less than 2.0 mm).

Moreover, at least part of the motor cortex 930 is between about 5.0 mm to about 10.0 mm from the inferior sagittal sinus 902. When the second endovascular carrier 108B carrying the second electrode array 102B is implanted within the inferior sagittal sinus 902, the intracorporeal target stimulated can also include a fornix 944 of the subject. The fornix 944 can be between about 10.0 mm to about 15.0 mm from the inferior sagittal sinus 902.

In further embodiments, the second endovascular carrier 108B carrying the second electrode array 102B can be implanted within a superficial cerebral vein. For example, the second endovascular carrier 108B carrying the second electrode array 102B can be implanted within at least one of a vein of Labbe 910, a vein of Trolard 912, a Sylvian vein 914, and a Rolandic vein 916.

In some embodiments, the second endovascular carrier 108B carrying the second electrode array 102B can be implanted within a deep cerebral vein. For example, the second endovascular carrier 108B carrying the second electrode array 102B can be implanted within at least one of a vein of Rosenthal 918, a vein of Galen 920, a superior thalamostriate vein 922, and an internal cerebral vein 926.

When the second endovascular carrier 108B carrying the second electrode array 102B is implanted within the vein of Rosenthal 918, the intracorporeal target stimulated can include at least one of the cerebellum 928, the anterior nucleus of thalamus 932, the centromedian nucleus of thalamus 934, the hippocampus 936, the subthalamic nucleus 938, and the caudal zone incerta 940. The vein of Rosenthal 918 can be between about 10.0 mm to about 15.0 mm from at least part of the cerebellum 928, the anterior nucleus of thalamus 932, and the centromedian nucleus of thalamus 934. The vein of Rosenthal 918 can be between about 5.0 mm to about 10.0 mm from at least part of the hippocampus 936, the subthalamic nucleus 938, and the caudal zone incerta 940.

When the second endovascular carrier 108B carrying the second electrode array 102B is implanted within the internal cerebral vein 926, the intracorporeal target stimulated can include at least one of the anterior nucleus of thalamus 932, the centromedian nucleus of thalamus 934, the hypothalamus 942, the fornix 944, and the caudal zone incerta 940. The internal cerebral vein 926 can be between about 10.0 mm to about 15.0 mm from at least part of the hypothalamus 942 and the caudal zone incerta 940. The internal cerebral vein 926 can be between about 5.0 mm to about 10.0 mm from at least part of the anterior nucleus of thalamus 932. The internal cerebral vein 926 can be between about 2.0 mm to about 5.0 mm from at least part of the fornix 944. The internal cerebral vein 926 can be adjacent to (i.e., separated by less than 2.0 mm from) the centromedian nucleus of thalamus 934.

When the second endovascular carrier 108B carrying the second electrode array 102B is implanted within the superior thalamostriate vein 922, the intracorporeal target stimulated can include at least one of the anterior nucleus of thalamus 932, the centromedian nucleus of thalamus 934, and the fornix 944. The superior thalamostriate vein 922 can be adjacent to (i.e., separated by less than 2.0 mm from) the anterior nucleus of thalamus 932, the centromedian nucleus of thalamus 934, and the fornix 944.

In certain embodiments, the second endovascular carrier 108B carrying the second electrode array 102B can also be implanted or configured to be implanted within a vessel extending through a hippocampus or amygdala of the subject.

In some embodiments, stimulating the intracorporeal target or the stimulation target via the second electrode array 102B can increase blood flow to the intracorporeal target or raise levels of certain neurotransmitters involved in suppressing seizure activity. Moreover, stimulating the intracorporeal target via the second electrode array 102B can also lead to sodium-channel inactivation (using high-frequency stimulation), long-term depression of certain neurotransmitters (using high-frequency stimulation), and/or glutamatergic depression (using both low-frequency and high-frequency stimulation).

For example, when stimulating cortical or cerebral targets, the electrical impulse can be bipolar with the voltage of the electrical impulse increased from 1V to 7 V in 0.25 V steps. The electrical impulse generated can have a pulse width of between 90 µS to about 540 µS, a frequency between about 3 Hz to 5 Hz in a low-frequency range, and a frequency between about 50 Hz to 130 Hz in a high-frequency range.

Although recording and stimulating using electrode arrays 102 coupled to different endovascular carriers 108 are discussed, it is contemplated by this disclosure that the same endovascular carrier (see, e.g., the endovascular carrier 214 shown in 2D) can carry both the first electrode array 102A and the second electrode array 102B. For example, an expandable stent or scaffold can carry both recording electrode arrays and stimulating electrode arrays on the same expandable stent or scaffold.

Figure 10:
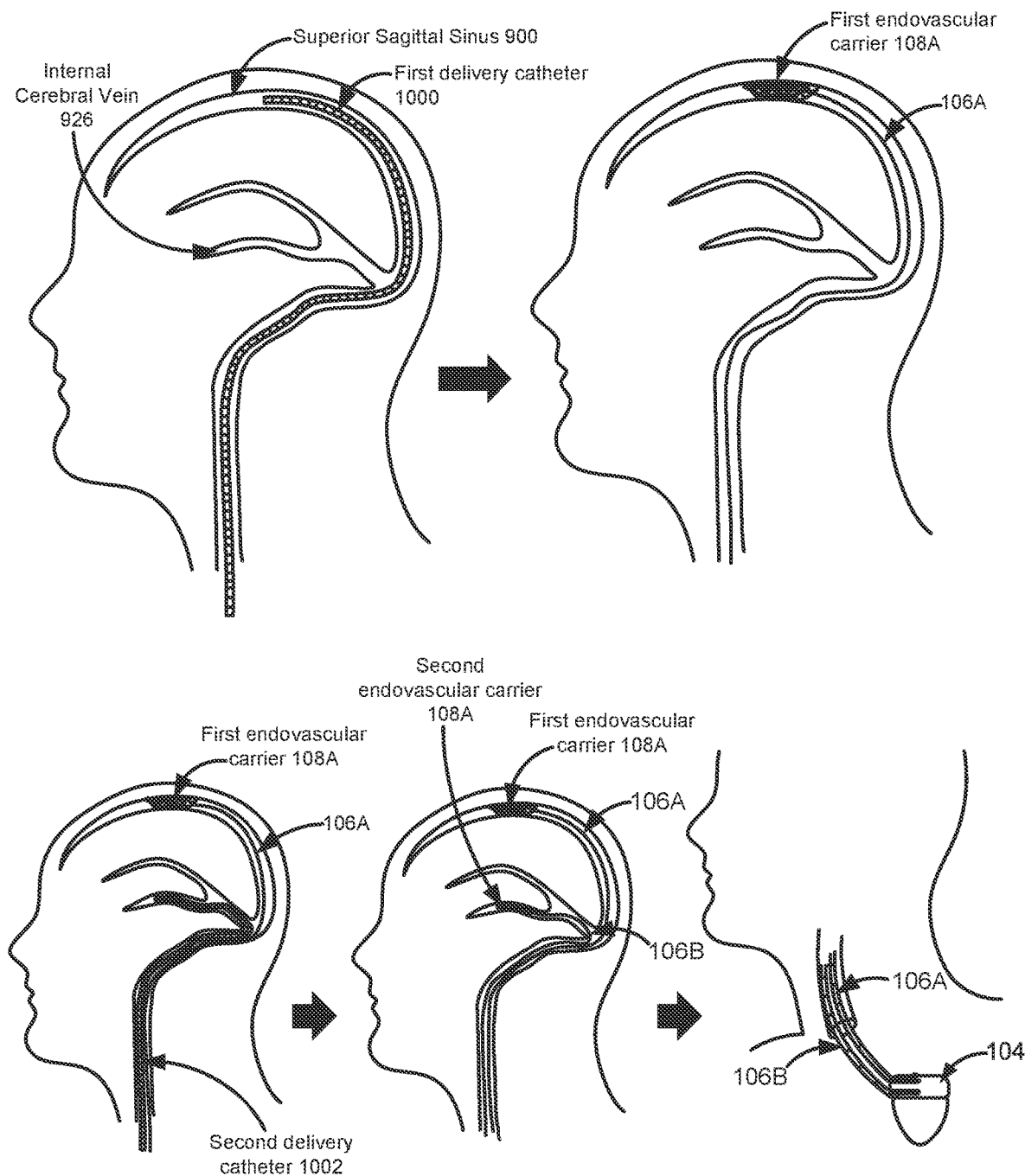
FIG. 10 illustrates one embodiment of a method of deploying or delivering endovascular carriers.

FIG. 10 illustrates one embodiment of a method of deploying or delivering the endovascular carriers 108 (e.g., the first endovascular carrier 108A and the second endovascular carrier 108B) to their respective implantation sites. Although the figures illustrate two endovascular carriers 108 being deployed, it is contemplated by this disclosure that similar apparatus or similar methods can also be used to deliver a singular endovascular carrier (see, e.g., endovascular carrier 214 of FIG. 2D) carrying separate electrode arrays 102 or three or more endovascular carriers.

As shown in FIG. 10, a first delivery catheter 1000 can be deployed through a jugular incision to the superior sagittal sinus 900. The first delivery catheter 1000 can be deployed under angiographic guidance. Although the superior sagittal sinus 900 is shown in the figures, it should be understood by one of ordinary skill in the art that the catheter and carriers can be deployed into any vein, sinus, or artery of the subject.

A first endovascular carrier 108A carrying a first electrode array 102A (not shown in FIG. 10, see FIG. 1) can be deployed or otherwise delivered through the first delivery catheter 1000. For example, the first endovascular carrier 108A can be a stent-electrode array 109 configured to self expand into position within the superior sagittal sinus 900.

In some embodiments, the first electrode array 102A coupled to the first endovascular carrier 108A can be used as a recording electrode array. In other embodiments, the first electrode array 102A can be used as a stimulating electrode array or both a recording electrode array and a stimulating electrode array. Once the first endovascular carrier 108A is positioned in place, the first delivery catheter 1000 can be removed from the vasculature of the subject.

FIG. 10 also illustrates that a second delivery catheter 1002 can be deployed through the same jugular incision to the internal cerebral vein 926 overlying the anterior nucleus of thalamus 932. The second delivery catheter 1002 can be deployed under angiographic guidance.

A second endovascular carrier 108B carrying a second electrode array 102B (not shown in FIG. 10, see FIG. 1) can be deployed or otherwise delivered through the second delivery catheter 1002. For example, the second endovascular carrier 108B can be a stent-electrode array 109 configured to self expand into position within the internal cerebral vein 926.

In some embodiments, the second electrode array 102B coupled to the second endovascular carrier 108B can be used as a stimulating electrode array. In other embodiments, the second electrode array 102B can be used as a recording electrode array or both a stimulating electrode array and a recording electrode array. Once the second endovascular carrier 108B is positioned in place, the second delivery catheter 1002 can be removed from the vasculature of the subject.

Moreover, as shown in FIG. 10, a first transmission lead 106A coupled to the first electrode array 102A on the first endovascular carrier 108A can extend through the neck of the subject (e.g., through a jugular vein) and a proximal end of the first transmission lead 106A can be inserted into a neuromodulation unit 104 (e.g., into a header portion 114, see, FIG. 1) implanted within the subject. In addition, a second transmission lead 106B coupled to the second electrode array 102B on the second endovascular carrier 108B can extend through the neck of the subject and a proximal end of the second transmission lead 106B can be inserted into the neuromodulation unit 104.

Figure 11:
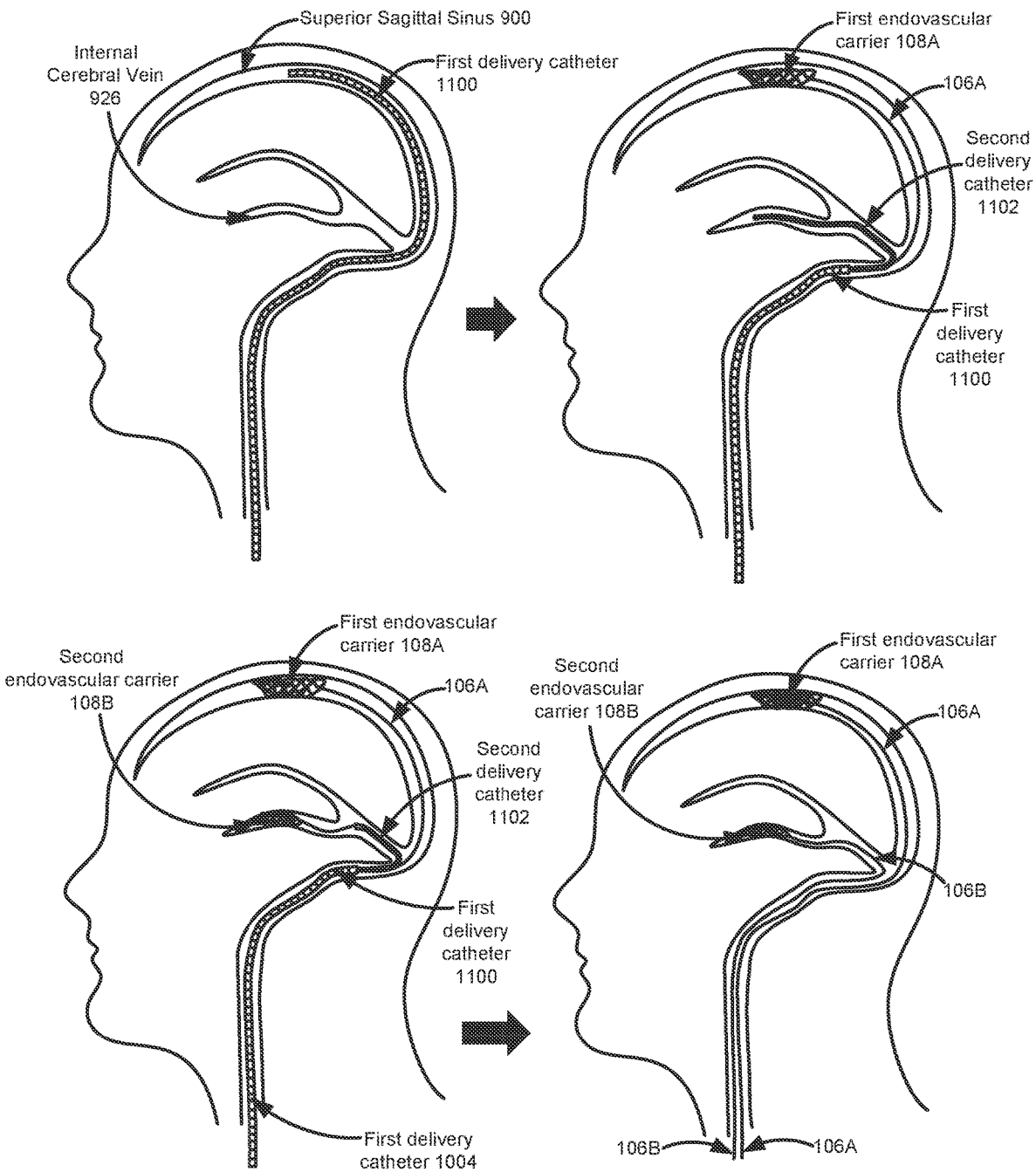
FIG. 11 illustrates another embodiment of a method of deploying or delivering the endovascular carriers.

FIG. 11 illustrates another embodiment of a method of deploying or delivering the endovascular carriers 108 (e.g., the first endovascular carrier 108A and the second endovascular carrier 108B) to their respective implantation sites. Although the figures illustrate two endovascular carriers 108 being deployed, it is contemplated by this disclosure that similar apparatus or similar methods can also be used to deliver a singular endovascular carrier (see, e.g., endovascular carrier 214 of FIG. 2D) carrying separate electrode arrays 102 or three or more endovascular carriers.

As shown in FIG. 11, a first delivery catheter 1100 can be deployed through a jugular incision to the superior sagittal sinus 900. The first delivery catheter 1100 can be deployed under angiographic guidance. Although the superior sagittal sinus 900 is shown in the figures, it should be understood by one of ordinary skill in the art that the catheter and carriers can be deployed into any vein, sinus, or artery of the subject.

A first endovascular carrier 108A carrying a first electrode array 102A (not shown in FIG. 11, see FIG. 1) can be deployed or otherwise delivered through the first delivery catheter 1100. For example, the first endovascular carrier 108A can be a stent-electrode array 109 configured to self expand into position within the superior sagittal sinus 900.

In some embodiments, the first electrode array 102A coupled to the first endovascular carrier 108A can be used as a recording electrode array. In other embodiments, the first electrode array 102A can be used as a stimulating electrode array or both a recording electrode array and a stimulating electrode array. Once the first endovascular carrier 108A is positioned in place, the first delivery catheter 1000 can be removed from the vasculature of the subject.

FIG. 11 also illustrates that the first delivery catheter 1100 can be retracted proximally and a second delivery catheter 1102 can be deployed through the retracted first delivery catheter 1100. The second delivery catheter 1002 can be deployed to the internal cerebral vein 926 overlying the anterior nucleus of thalamus 932. The second delivery catheter 1002 can be deployed under angiographic guidance.

A second endovascular carrier 108B carrying a second electrode array 102B (not shown in FIG. 11, see FIG. 1) can be deployed or otherwise delivered through the second delivery catheter 1002. For example, the second endovascular carrier 108B can be a stent-electrode array 109 configured to self expand into position within the internal cerebral vein 926.

In some embodiments, the second electrode array 102B coupled to the second endovascular carrier 108B can be used as a stimulating electrode array. In other embodiments, the second electrode array 102B can be used as a recording electrode array or both a stimulating electrode array and a recording electrode array. Once the second endovascular carrier 108B is positioned in place, the second delivery catheter 1102 can be removed from the vasculature of the subject.

A first transmission lead 106A coupled to the first electrode array 102A on the first endovascular carrier 108A can extend through the neck of the subject (e.g., through a jugular vein) and a proximal end of the first transmission lead 106A can be inserted into a neuromodulation unit 104 (e.g., into a header portion 114, see, FIG. 1) implanted within the subject. In addition, a second transmission lead 106B coupled to the second electrode array 102B on the second endovascular carrier 108B can extend through the neck of the subject and a proximal end of the second transmission lead 106B can be inserted into the neuromodulation unit 104.

Figure 12:
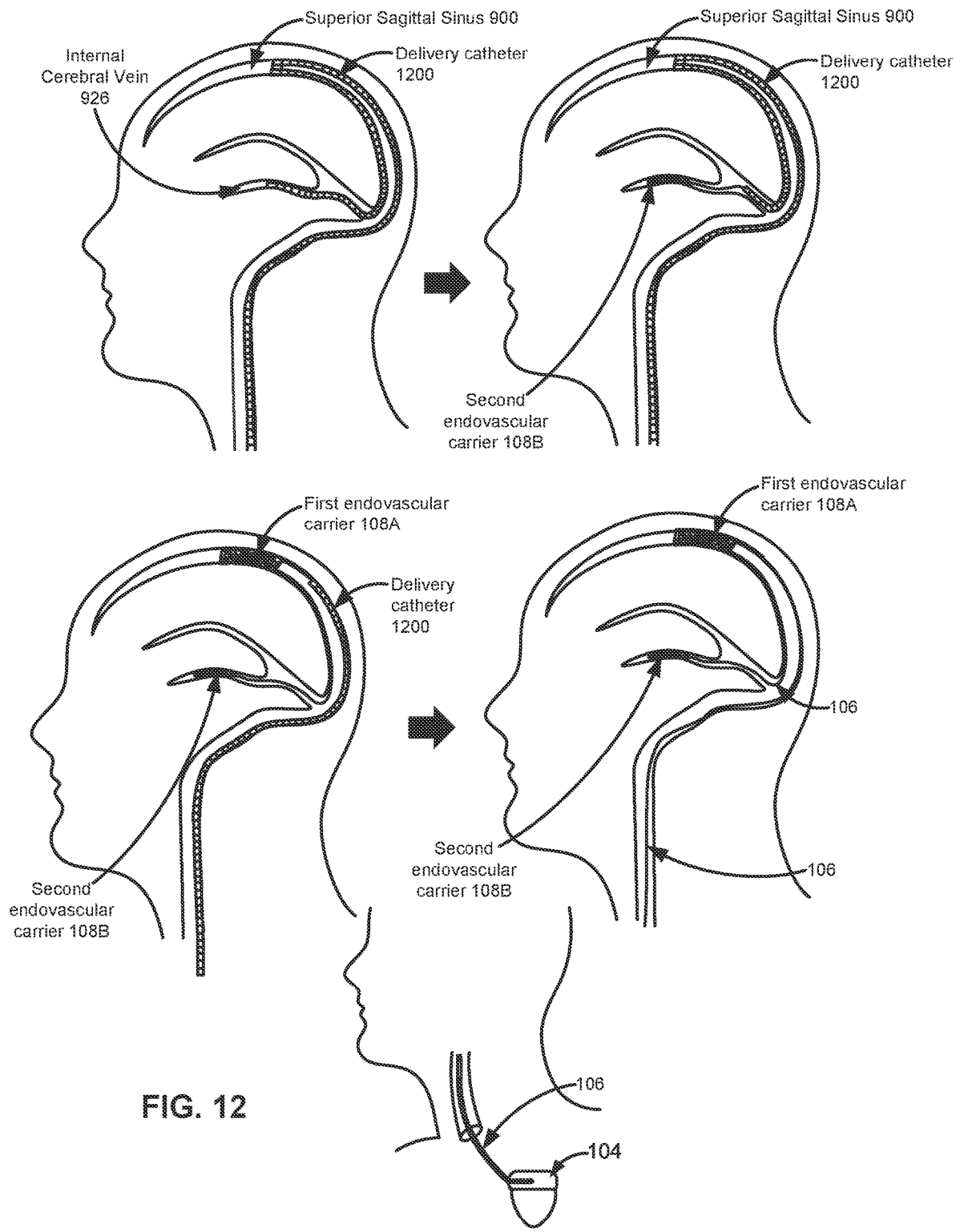
FIG. 12 illustrates yet another embodiment of a method of deploying or delivering the endovascular carriers.

FIG. 12 illustrates another embodiment of a method of deploying or delivering the endovascular carriers 108 (e.g., the first endovascular carrier 108A and the second endovascular carrier 108B) to their respective implantation sites. Although the figures illustrate two endovascular carriers 108 being deployed, it is contemplated by this disclosure that similar apparatus or similar methods can also be used to deliver three or more endovascular carriers.

As shown in FIG. 12, a delivery catheter 1200 can be deployed through a jugular incision to the superior sagittal sinus 900 and then continuing on to the internal cerebral vein 926 overlying the anterior nucleus of thalamus 932. The delivery catheter 1200 can be deployed under angiographic guidance.

Although the superior sagittal sinus 900 is shown in the figures, it should be understood by one of ordinary skill in the art that the catheter and carriers can be deployed into any vein, sinus, or artery of the subject.

The second endovascular carrier 108B carrying the second electrode array 102B (not shown in FIG. 12, see FIG. 1) can be deployed or otherwise delivered through the delivery catheter 1200. For example, the second endovascular carrier 108B can be a stent-electrode array 109 configured to self expand into position within the internal cerebral vein 926.

In some embodiments, the second electrode array 102B coupled to the second endovascular carrier 108B can be used as a recording electrode array. In other embodiments, the second electrode array 102B can be used as a stimulating electrode array or a recording electrode array and a stimulating electrode array. Once the second endovascular carrier 108B is positioned in place, the delivery catheter 1200 can be retracted until the distal end of the delivery catheter 1200 is in place to deploy the first endovascular carrier 108A into the superior sagittal sinus 900 of the subject. The first endovascular carrier 108A can carry the first electrode array 102A (not shown in FIG. 12, see FIG. 1). The first endovascular carrier 108A can be a stent-electrode array 109 configured to self expand into position within the superior sagittal sinus 900.

In some embodiments, the first electrode array 102A coupled to the first endovascular carrier 108A can be used as a stimulating electrode array. In other embodiments, the first electrode array 102A can be used as a recording electrode array or both a stimulating electrode array and a recording electrode array. Once the first endovascular carrier 108A is positioned in place, the delivery catheter 1200 can be removed from the vasculature of the subject.

Retracting the delivery catheter 1200 can expose a singular transmission lead 106 connecting the first endovascular carrier 108A to the second endovascular carrier 108B. The singular transmission lead 106 can extend through the neck of the subject (e.g., through a jugular vein) and a proximal end of the transmission lead 106 can be inserted into a neuromodulation unit 104 (e.g., into a header portion 114, see, FIG. 1) implanted within the subject.

Figure 13:
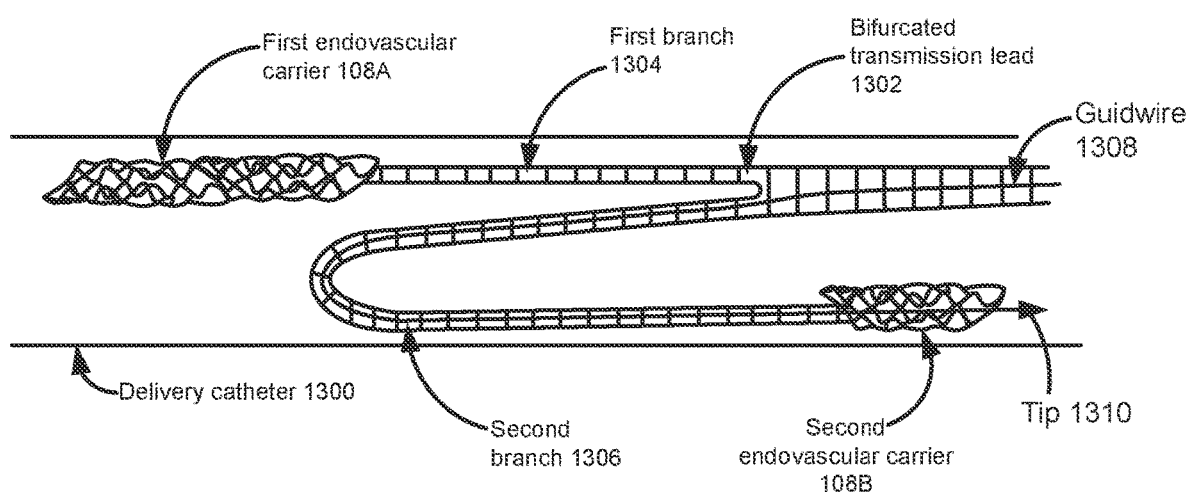
FIG. 13 illustrates an embodiment of a delivery catheter comprising a bifurcated transmission lead.

FIG. 13 illustrates an embodiment of a delivery catheter 1300 comprising a first endovascular carrier 108A and a second endovascular carrier 108B connected by a bifurcated transmission lead 1302. As shown in FIG. 13, a first branch 1304 of the bifurcated transmission lead 1302 can be connected or coupled to the first endovascular carrier 108A and a second branch 1306 of the bifurcated transmission lead 1302 can be connected or coupled to the second endovascular carrier 108B. At least one guidewire 1308 can extend alongside at least one of the branches of the bifurcated transmission lead 1302. The guidewire 1308 can extend through a lumen of one of the endovascular carriers 108 (e.g., the second endovascular carrier 108B) and be detachably coupled to a tip 1310 of the endovascular carrier 108.

Another method of deploying or delivering the endovascular carriers 108 (e.g., the first endovascular carrier 108A and the second endovascular carrier 108B) to their respective implantation sites can comprise deploying the delivery catheter 1300 through a jugular incision to the superior sagittal sinus 900. The delivery catheter 1300 can be deployed under angiographic guidance.

A first endovascular carrier 108A carrying a first electrode array 102A (not shown in FIG. 13, see FIG. 1) can be deployed or otherwise delivered through the delivery catheter 1300. For example, the first endovascular carrier 108A can be a stent-electrode array 109 configured to self expand into position within the superior sagittal sinus 900.

In some embodiments, the first electrode array 102A coupled to the first endovascular carrier 108A can be used as a recording electrode array. In other embodiments, the first electrode array 102A can be used as a stimulating electrode array or both a recording electrode array and a stimulating electrode array. Once the first endovascular carrier 108A is positioned in place, the delivery catheter 1300 can be retracted proximally and a second endovascular carrier 108B carrying a second electrode array 102B (not shown in FIG. 13, see FIG. 1) can be deployed through the retracted delivery catheter 1300 into a second implantation site (e.g., the internal cerebral vein 926 overlying the anterior nucleus of thalamus 932 of the subject). The guidewire 1308 can be used to guide the second endovascular carrier 108 into place within the second implantation site.

For example, the second endovascular carrier 108B can be a stent-electrode array 109 configured to self expand into position within a deployed vessel such as the internal cerebral vein 926. In some embodiments, the second electrode array 102B coupled to the second endovascular carrier 108B can be used as a stimulating electrode array. In other embodiments, the second electrode array 102B can be used as a recording electrode array or both a stimulating electrode array and a recording electrode array. Once the second endovascular carrier 108B is positioned in place, the delivery catheter 1300 and the guidewire 1308 can be removed from the vasculature of the subject.

Retracting the delivery catheter 1300 can expose the bifurcated transmission lead 1302 connecting the first endovascular carrier 108A to the second endovascular carrier 108B. The transmission lead 1302 can extend through the neck of the subject (e.g., through a jugular vein) and a proximal end of the transmission lead 1302 can be inserted into a neuromodulation unit 104 (e.g., into a header portion 114, see, FIG. 1) implanted within the subject.

One technical advantage of the closed-loop neuromodulation system 100 disclosed herein is that the system 100 can be delivered through a minimally invasive procedure, via angiography, to a vessel near an intracorporeal/stimulation target (e.g., the vagus nerve) without physically contacting or potentially causing damage to the intracorporeal/stimulation target (e.g., causing damage to the vagus nerve).

Another technical advantage of the neuromodulation system 100 disclosed herein is that when the first endovascular carrier 108A (carrying the first electrode array 102A or the recording electrode array) is implanted within a cortical/cerebral vein or sinus and the second endovascular carrier 108B (carrying the second electrode array 10B or the stimulating electrode array) is implanted within a cortical/cerebral vein or sinus or within a vein or artery superior to the skull of the subject, the skull of the subject can act as a protective casing that protects the carriers from potentially destructive external forces and improves the electrophysiological signals detected or recorded.

Yet another technical advantage of the neuromodulation system 100 disclosed herein is that the system 100 can provide a closed-loop or responsive stimulation whereby an electrophysiological signal from the subject is detected or otherwise acquired and used as the impetus to trigger the electrical stimulation. An added advantage of the system operating in a closed-loop or responsive mode is that the battery life of the various electronic components of the system can be extended such that such electronic components are only activated when a seizure is imminent or when the subject is observed to be in a high seizure risk state.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to +0.1%, +1%, +5%, or +10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

We claim:

1. A method of treating epilepsy, comprising:
   detecting, using a first electrode array, an electrophysiological signal of a subject, wherein the first electrode array is coupled to a first endovascular carrier implanted within the subject in at least one of a superior sagittal sinus, an inferior sagittal sinus, a sigmoid sinus, a transverse sinus, and a straight sinus of the subject;
   analyzing the electrophysiological signal using a neuromodulation unit implanted within the subject and electrically coupled to the first electrode array; and
   stimulating an intracorporeal target of the subject using a second electrode array in response to the electrophysiological signal detected, wherein the second electrode array is electrically coupled to the neuromodulation unit, and wherein the second electrode array is coupled to a second endovascular carrier implanted within at least one of a vein of Labbe, a vein of Trolard, a Sylvian vein, and a Rolandic vein of the subject.

2. The method of claim 1, wherein the neuromodulation unit is implanted within a forearm of the subject.

3. The method of claim 2, wherein stimulating the intracorporeal target further comprises generating an electrical impulse using a pulse generator of the neuromodulation unit, and wherein the pulse generator is powered and activated by an extracorporeal device, and wherein the extracorporeal device is provided as part of an armband.

4. The method of claim 1, wherein at least one of the first endovascular carrier and the second endovascular carrier is an endovascular scaffold comprising an electrode array coupled to the endovascular scaffold.

5. The method of claim 1, wherein stimulating the intracorporeal target further comprises generating an electrical impulse using a pulse generator of the neuromodulation unit, and wherein the pulse generator is configured to generate the electrical impulse by increasing a current amplitude of the electrical impulse from 0 mA to up to 10 mA in 0.1 mA steps and increasing a voltage of the electrical impulse from 0 V to up to 10 V in 0.25 V steps, wherein a pulse width of the electrical impulse generated is configured to be between 25 µS to about 600 µS, and wherein a frequency of the electrical impulse generated is configured to be between 1 Hz and 400 Hz.

* * * * *